(12) United States Patent
Emmanouilidis

(10) Patent No.: US 9,993,249 B2
(45) Date of Patent: Jun. 12, 2018

(54) DEVICE COMBINATION FOR CONNECTING HOLLOW ORGANS (ANASTOMOSIS)

(71) Applicant: MEDIZINISCHE HOCHSCHULE HANNOVER, Hannover (DE)

(72) Inventor: Nikos Emmanouilidis, Garbsen (DE)

(73) Assignee: Medizinische Hochschule Hannover, Hannover (DE)

( * ) Notice: Subject to any disclaimer, the term of this patent is extended or adjusted under 35 U.S.C. 154(b) by 455 days.

(21) Appl. No.: 14/353,669

(22) PCT Filed: Oct. 26, 2012

(86) PCT No.: PCT/EP2012/071240
§ 371 (c)(1),
(2) Date: Apr. 23, 2014

(87) PCT Pub. No.: WO2013/060832
PCT Pub. Date: May 2, 2013

(65) Prior Publication Data
US 2014/0350566 A1    Nov. 27, 2014

(30) Foreign Application Priority Data
Oct. 26, 2011    (DE) .................. 10 2011 054 821

(51) Int. Cl.
*A61B 17/10* (2006.01)
*A61B 17/11* (2006.01)
(Continued)

(52) U.S. Cl.
CPC .... *A61B 17/1114* (2013.01); *A61B 17/00234* (2013.01); *A61B 17/1155* (2013.01);
(Continued)

(58) Field of Classification Search
CPC ......... A61B 17/1114; A61B 2017/1117; A61B 2017/1121; A61B 2017/1125;
(Continued)

(56) References Cited

U.S. PATENT DOCUMENTS 4,703,887 A  *  11/1987  Clanton ............... A61B 17/115
                                                        227/19
7,285,125 B2 *  10/2007  Viola .................... A61B 17/11
                                                       128/898
(Continued)

FOREIGN PATENT DOCUMENTS

DE         693 14 848      5/1993
DE         43 27 233       8/1993
(Continued)

*Primary Examiner* — Katrina Stransky
*Assistant Examiner* — Kankindi Rwego
(74) *Attorney, Agent, or Firm* — Whitham, Curtis & Cook, P.C.

(57) ABSTRACT

The invention relates to a surgical device (100) designed to be inserted into a stump of a hollow organ (40) of a person or animal in order to prepare a circular anastomosis, wherein the device (100) is designed without a stapling unit for producing a surgical stapled seam, wherein the device (100) has an instrument shaft (120) having a handle section (121, 300) and, at the end of time instrument shaft (120) away from the handle section (121, 300), a head section (130) that is or can be coupled to the instrument shaft (120) by means of a detachable coupling (113), wherein the handle section (121, 300) is designed for a user to hold the device (100), wherein the head section (130) has at least one first molded body (109) and a counter-pressure plate (111) of a surgical circular stapling device (160) connected to the first molded body (109), wherein the surgical device has fu least one first molded body (109) and one second molded body (108) between the handle section and the counter-pressure plate, the second molded body being arranged immediately adja- (Continued)

cent to the first molded body (109), wherein a third cross-section reduction (122), which is used as a cutting aid for severing a part of the hollow organ (40) and which rotates about the longitudinal axis of the device (100), is present between the first molded body (109) and the second molded body (108), at which third cross-section reduction the cross-section of the device (100) is reduced relative to the cross-section of the first and second molded bodies (108, 109), wherein the first and second molded body (108, 109) have rounded transitions without edges at the transitions to the third cross-section reduction (122).

20 Claims, 18 Drawing Sheets

(51) Int. Cl.
| | |
|---|---|
| *A61B 17/115* | (2006.01) |
| *A61B 17/12* | (2006.01) |
| *A61B 17/00* | (2006.01) |
| *A61B 17/04* | (2006.01) |
| *A61B 17/072* | (2006.01) |
| *A61B 18/14* | (2006.01) |

(52) U.S. Cl.
CPC .... *A61B 17/12013* (2013.01); *A61B 17/0485* (2013.01); *A61B 17/07207* (2013.01); *A61B 2017/0046* (2013.01); *A61B 2017/00278* (2013.01); *A61B 2017/00358* (2013.01); *A61B 2017/00477* (2013.01); *A61B 2017/1135* (2013.01); *A61B 2018/141* (2013.01)

(58) Field of Classification Search
CPC ............ A61B 17/1128; A61B 17/1132; A61B 17/1135; A61B 17/1139; A61B 17/1142; A61B 17/1155
See application file for complete search history.

(56) References Cited

U.S. PATENT DOCUMENTS

| | | | | |
|---|---|---|---|---|
| 7,303,106 B2* | 12/2007 | Milliman | ............. | A61B 17/115 227/175.1 |
| 2010/0213239 A1* | 8/2010 | Rebuffat | ............. | A61B 17/115 227/180.1 |
| 2010/0301098 A1* | 12/2010 | Kostrzewski | ........ | A61B 17/115 227/179.1 |

FOREIGN PATENT DOCUMENTS

| | | |
|---|---|---|
| EP | 0570915 | 11/1993 |
| EP | 2153781 | 2/2010 |
| WO | WO2004/112583 | 12/2004 |
| WO | WO2010/063313 | 6/2010 |

* cited by examiner

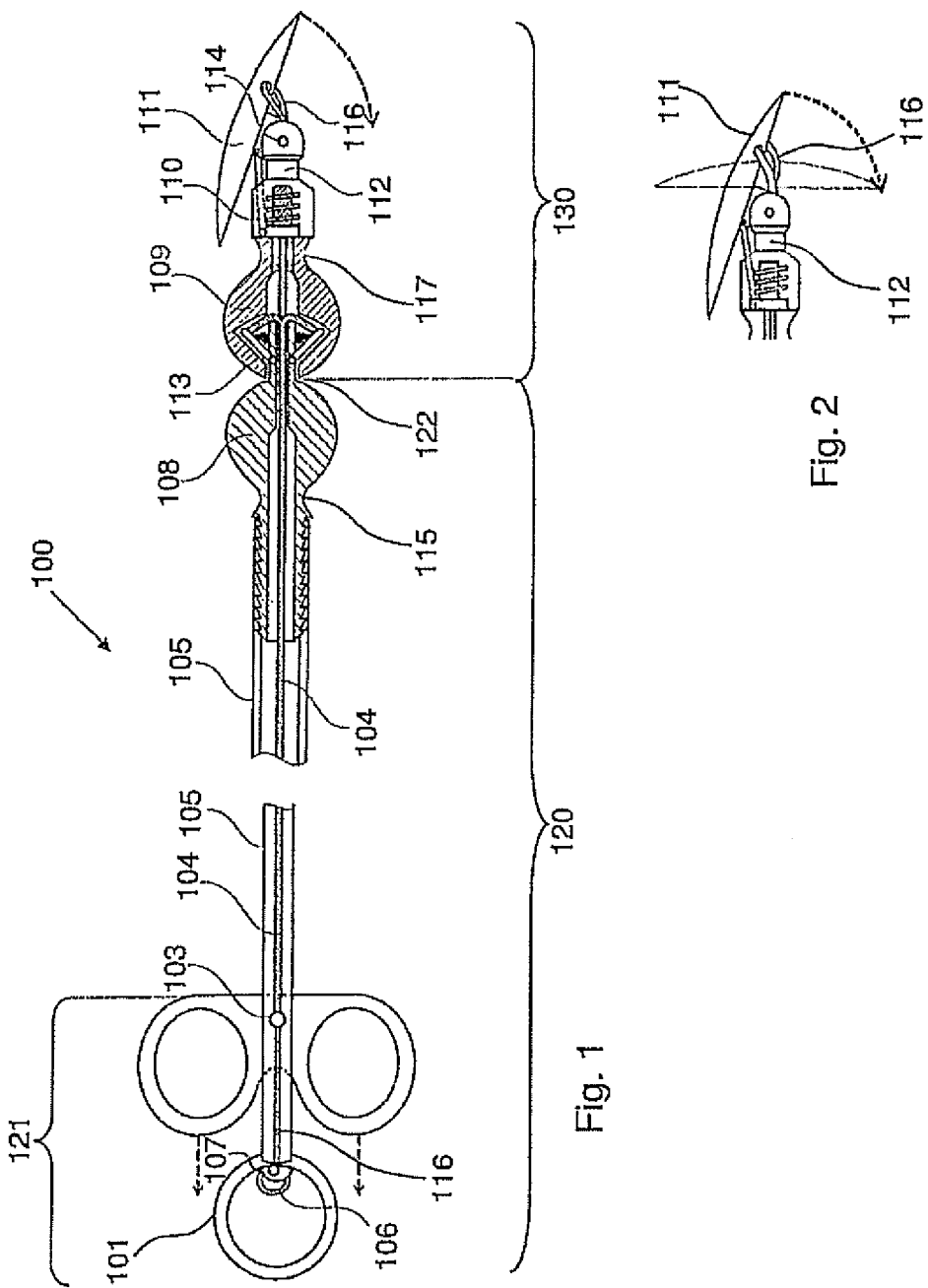

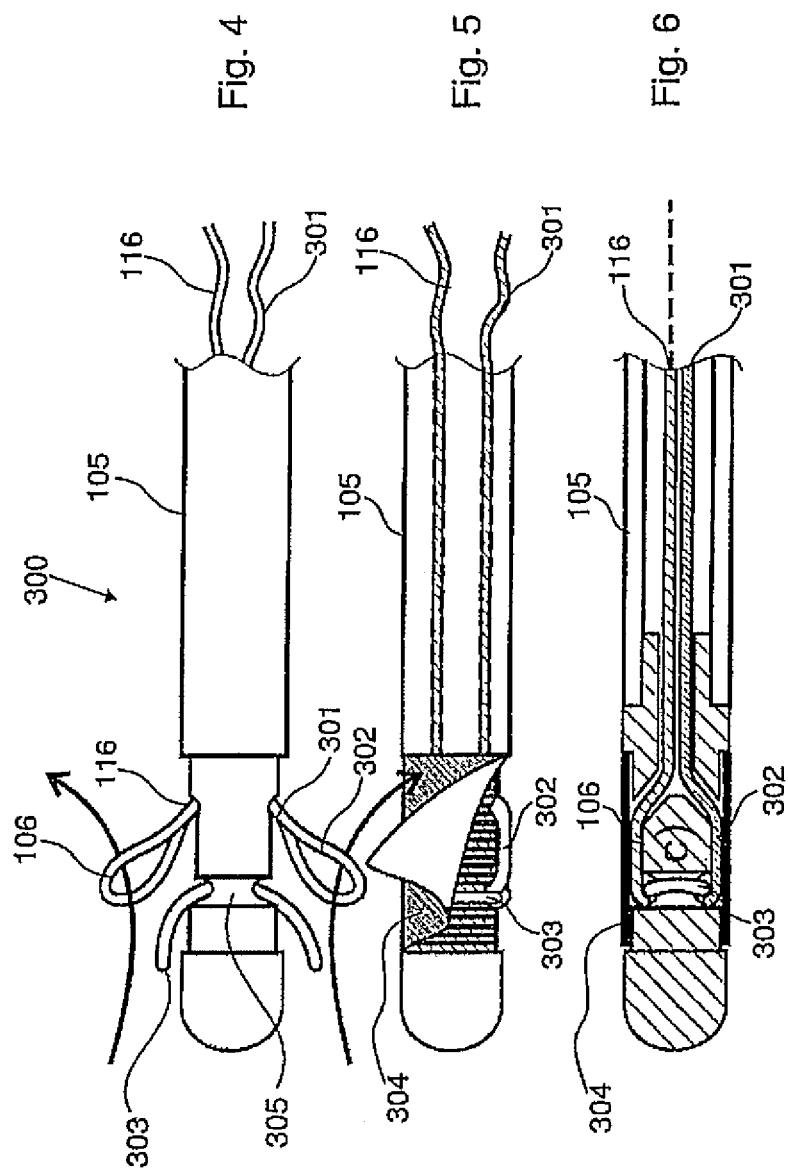

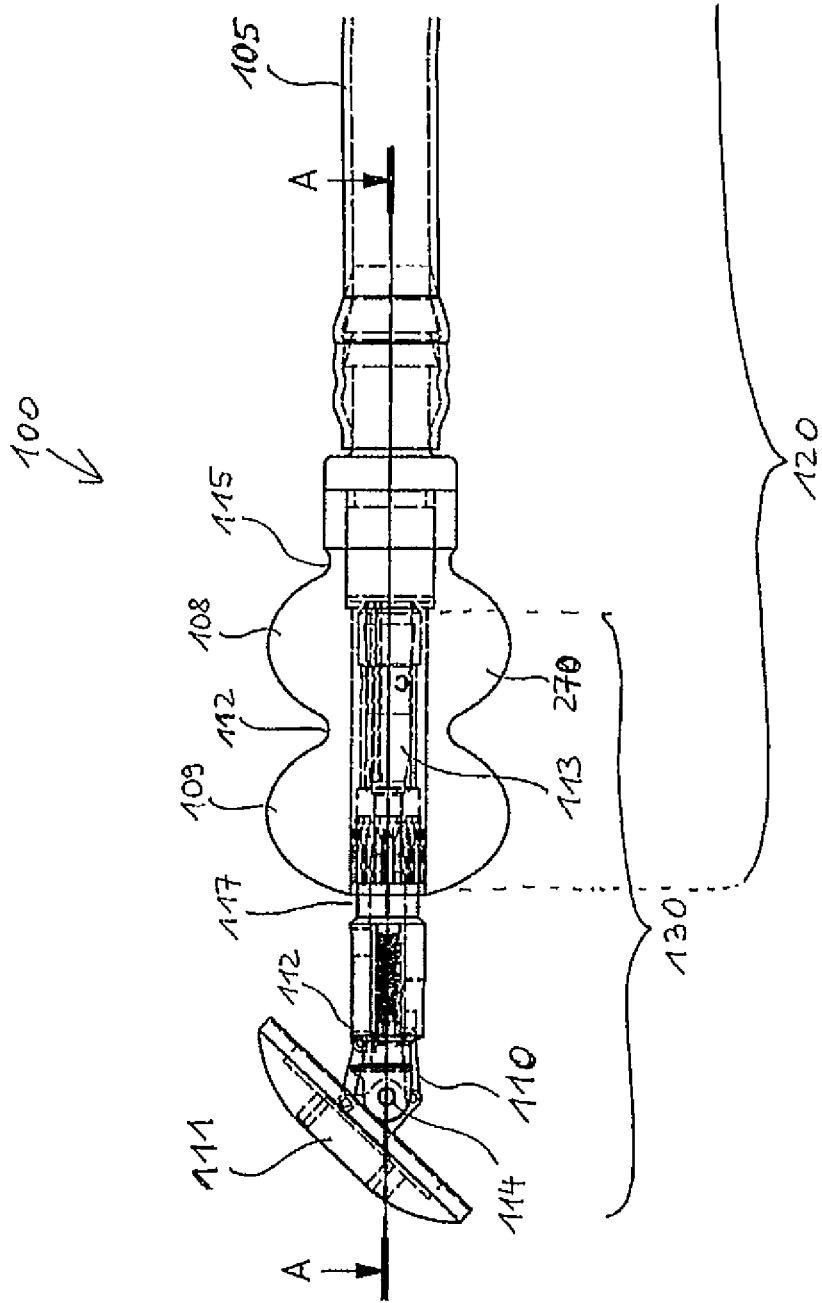

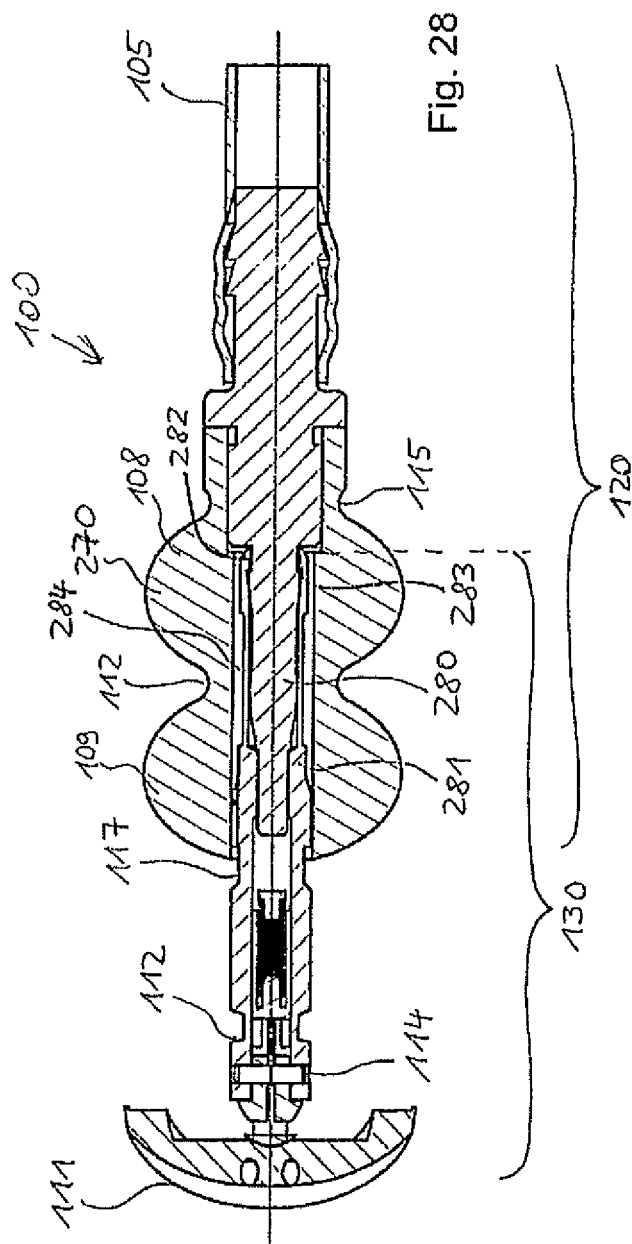
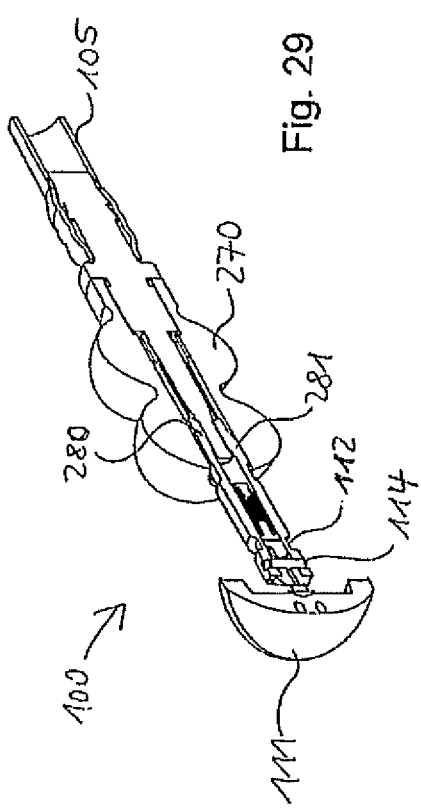

DEVICE COMBINATION FOR CONNECTING HOLLOW ORGANS (ANASTOMOSIS)

The invention relates to a surgical appliance designed to be introduced into a stump of a hollow organ of a human or animal so as to prepare for a circular anastomosis, in accordance with claim 1. The invention further relates to a surgical resection device for performing a circular resection of a stump of a hollow organ of a human or animal so as to prepare for a circular anastomosis, in accordance with claim 13. The invention also relates to a kit consisting of the aforementioned surgical appliance and of the aforementioned surgical resection device, in accordance with claim 16. Moreover, the invention relates to a surgical circular stapling appliance for performing a circular anastomosis of a hollow organ of a human or animal, in accordance with claim 19.

The invention generally concerns assistance in the preparation and performance of a circular anastomosis of hollow organs of a human or animal in surgical interventions, particularly in the gastrointestinal tract. To treat tumors or inflammatory diseases, it is in some cases necessary to remove all or part of a hollow organ such as the stomach, the esophagus, the small intestine or the large intestine. To do so, the hollow organ is firstly separated. It is important to ensure that the two stumps of the hollow organ are well closed in order to avoid escape of body fluids, e.g. into the abdominal cavity. Escape of body fluids could lead to serious complications, for example sepsis. In order to close the stump, the latter is closed transversely using a stapling appliance, e.g. a linear endostapler. After the tissue that is to be removed has been removed, the organ stumps are joined together again. This is mostly done using what is known as a circular endostapler. A circular endostapler of this kind is known from US 20110011916 A1, for example.

A problem is that the circular stapled suture of the circular endostapler crosses the transverse stapled suture previously applied for the organ closure, at both ends of said stapled suture. Since the tissue at these sites is already thickened and compacted by the transverse stapled suture, it is not always possible to ensure a uniform pressure of the tissue and a uniform deformation of the sutures across the entire circular stapled suture. This can therefore lead to inadequate closure between the organ stumps. A further problem is that the transverse suture also impedes the function of the circular scalpel of the circular endostapler, such that the circular scalpel in many cases does not completely cut through the transverse suture. In this case, the circular stapled suture may be damaged when withdrawing the circular endostapler.

The object of the invention is therefore to provide possibilities for improved preparation and performance of a circular anastomosis.

According to claim 1, this object is achieved by a surgical appliance designed to be introduced into a stump of a hollow organ of a human or animal so as to prepare for a circular anastomosis, wherein the appliance is designed without a stapling unit for generating a surgical stapled suture, wherein the appliance has an instrument shaft with a grip portion and, at the end of the instrument shaft remote from the grip portion, a head portion which is coupled or can be coupled to the instrument shaft via a releasable coupling, wherein the grip portion is designed to allow the appliance to be held by a user, wherein the head portion has at least a first shaped body and a counter-pressure plate of a surgical circular stapler connected to the first shaped body, wherein the surgical appliance has, between the grip portion and the counter-pressure plate, at least a first shaped body and a second shaped body, which is arranged immediately adjacent to the first shaped body, wherein a third cross-sectional reduction, which is used as a cutting aid for severing a part of the hollow organ and which encircles the longitudinal axis of the appliance, is present between the first shaped body and the second shaped body, at which third cross-sectional reduction the cross section of the appliance is reduced in relation to the cross section of the first and second shaped bodies, wherein the first and second shaped bodies have, at the transitions to the third cross-sectional reduction, rounded transitions without edges. A surgical appliance of this kind serves for the preparation of a circular anastomosis, but not for the actual performance of the anastomosis, i.e. the production of the connection between the organ stumps by the circular stapler. The surgical appliance is therefore advantageously designed without a stapling unit for producing a surgical stapled suture. The stump of the hollow organ can be closed free of sutures by the head portion. This has the advantage that it is possible to dispense entirely with the previously provided transverse suture for closing the organ stump. The associated problems are therefore also dispensed with. Instead, the organ stump can be closed by the head portion without a suture. For this purpose, a thread loop, for example, or a tensioning band, for example in the manner of a cable binder, can be secured around the organ stump in the area between the first shaped body and the counter-pressure plate on the head portion. In this way, the organ stump is safely closed without a suture.

A further advantage is that a third cross-sectional reduction, which is used as a cutting aid for severing a part of the hollow organ and which encircles the longitudinal axis of the appliance, is present between the first shaped body and the second shaped body, at which third cross-sectional reduction the cross section of the appliance is reduced in relation to the cross section of the first and second shaped bodies, and that the first and second shaped bodies have, at the transitions to the third cross-sectional reduction, rounded transitions without edges. By means of the first and second shaped bodies emerging from the organ, this allows a user to quickly find the cutting position in the area of the third cross-sectional reduction. The third cross-sectional reduction can advantageously form a centering groove for an electric loop of a surgical resection device. In addition, gentle transitions from the shaped bodies to the third cross-sectional reduction are permitted, such that tearing of the tissue can be avoided. In particular, sudden changes in cross section can be avoided.

According to an advantageous development of the invention, the first shaped body is part of the head portion. The first shaped body can, in particular, be connected to or formed in one piece with the head portion even in the state when the head portion is uncoupled from the instrument shaft (120). This allows the head portion on the other side of the counter-pressure plate to be made relatively slender and without protruding parts. This advantageously permits a simple coupling of a surgical circular stapler for producing the circular stapled suture.

According to an advantageous development of the invention, the first shaped body is part of the instrument shaft. The first shaped body can in particular be connected to or formed in one piece with the instrument shaft, even in the state when the head portion is uncoupled from the instrument shaft. This has the advantage that the first shaped body can be used to close the organ stump.

According to an advantageous development of the invention, the first and second shaped bodies are formed in one piece as a common component. This permits particularly cost-effective production of the surgical appliance, such that it may also conceivably be used as a disposable article. In the one-piece design of the two shaped bodies as a common component, this component can be rigidly connected to the instrument shaft. Centrally, and oriented in the longitudinal axis, the portion of this component has a tubular channel, into which, in the axial center thereof, a longitudinally oriented prong in turn protrudes. This prong serves for coupling the head portion, wherein the coupling can be effected, for example, by a combination of rotationally symmetrical folds on the prong and a corresponding shaping of the sleeve of the head portion as elongate spring plates which at the ends engage in the folds on the prong. Release and also coupling of the head portion could be obtained by overcoming the spring resistance of the spring plates. Moreover, the organ stump would be closed, and at the same time fixed on the sleeve of the head portion, by means of a thread loop, for example, or a tensioning band, for example in the manner of a cable binder, while the opposite organ stump would be fixed on the instrument shaft, for example by a thread loop or a tensioning band, for example in the manner of a cable binder. Between the two fixing loops or tensioning bands, the one-piece shaped body would, according to its increase in cross section, support the tissue of the organ that is to be separated. Centrally between the two fixing loops or tensioning bands, the organ supported in the longitudinal direction could then be separated across the area of the central cross-sectional reduction of the shaped body, e.g. by using an incandescent loop. In the subsequent separation of the headpiece from the instrument shaft by axially pulling and overcoming the spring resistance, one organ stump together with the one-piece shaped body would remain on the instrument shaft and be removed jointly. Excess tissue of the resection margin on the remaining stump with a width corresponding to the distance between the first and second cross-sectional reductions could then be stripped off without difficulty from the shaped body. The remaining organ stump, which is used to restore the passage, would then be fixed by fixing loop or tensioning band on the sleeve of the headpiece.

According to an advantageous development of the invention, the first shaped body is designed for suture-free closure of the stump of the hollow organ, wherein the head portion has, between the first shaped body and the counter-pressure plate, a first cross-sectional reduction which encircles a longitudinal axis of the head portion and at which the cross section of the head portion decreases starting from the first shaped body in the direction of the counter-pressure plate, wherein the counter-pressure plate in turn has a greater cross section than the area of the first cross-sectional reduction, and wherein the length of the first shaped body in the direction of the longitudinal axis of the head portion is greater than the length of the first cross-sectional reduction in the same direction. As a result of the first cross-sectional reduction, the head portion remains at a defined location provided for it in the organ stump and closes the latter via the first shaped body. In particular, the first shaped body, in the direction of the longitudinal axis of the appliance, has a greater length than the first cross-sectional reduction. This allows the head portion, and in particular the first shaped body, to be formed in such a way as to avoid transitions, between the first shaped body and the first cross-sectional reduction, having small radii or sudden changes in cross section. The first shaped body can therefore be designed with a gentle, uniform transition to the first cross-sectional reduction. This has the advantage that the organ tissue, fixed in the first cross-sectional reduction by means of a thread loop or a tensioning band for example, is tensioned only to such an extent that tearing of the tissue can be avoided. By contrast, there would be a danger of the tissue tearing, for example, in the case of an abrupt transition from the first shaped body to the first cross-sectional reduction.

A further advantage is that a certain distance between the first shaped body and the counter-pressure plate is created by the first cross-sectional reduction, such that the counter-pressure plate is arranged at a certain distance from the first shaped body. Since the counter-pressure plate for producing the for example one or two circular stapled sutures must have a certain minimum diameter, it is expedient if there is a certain distance to the first shaped body, such that the tissue fixed in the first cross-sectional reduction does not have to be excessively tensioned.

An already complete and secure closure of the organ stump can be performed by means of the head portion, such that surgical complications caused by body fluids accidentally entering and leaving the organ stump can be reliably avoided.

The invention can advantageously be used for the removal of diseased organ parts in the gastrointestinal tract or for the treatment of obesity by reducing the size of the stomach.

According to an advantageous development of the invention, when the head portion is coupled to the instrument shaft, the counter-pressure plate on the head portion is arranged behind the first shaped body, as seen from the instrument shaft.

According to an advantageous development of the invention, the instrument shaft and/or the grip portion has a trigger mechanism whose actuation allows the releasable coupling to be released by remote control from the instrument shaft or grip portion, such that the instrument shaft can be removed from the head portion. By virtue of the fact that the releasable coupling can be released by remote control from the instrument shaft or grip portion, the instrument shaft can be removed from the head portion, such that the head portion can remain in the stump of the hollow organ that is to be at least temporarily closed. The releasable coupling in particular also permits a renewed connection of the head portion to the instrument shaft, e.g. if this should prove necessary during the operation. In this way, the surgical appliance or the instrument shaft thereof can be re-used intra-operatively, e.g. if a modified placement of the head portion is necessary.

The releasable coupling can advantageously be obtained in different ways. In one embodiment of the invention, the releasable coupling has retaining brackets which can be spread open by spring force and which, when the instrument shaft is coupled to the head portion, are arranged in a correspondingly shaped inner hollow space of the head portion. The retaining brackets can be drawn together counter to the spring force by the release mechanism and are then oriented approximately flush with the longitudinal direction of the instrument shaft. In this state, the retaining brackets can be removed from the hollow space of the head portion or introduced therein. With the release mechanism unactuated, the spring force causes an unfolding of the retaining elements, which then fix the instrument shaft on the head portion when the retaining elements are arranged in the hollow space of the head portion. In another advantageous embodiment, the releasable coupling mechanism has, instead of the aforementioned retaining brackets on the end area of the instrument shaft connectable to the head portion, an expandable balloon, e.g. in the manner of a balloon catheter. A Fogarty catheter can be used, for example. For fixing the instrument shaft on the head portion, the balloon is introduced into the aforementioned inner hollow space of the head portion and is then expanded, e.g. by being filled with liquid. The balloon is emptied in order to release the coupling. In another advantageous embodiment of the invention, the releasable coupling has an electrically actuatable magnet coupling, e.g. with an electromagnet which is arranged on the instrument shaft in the end area and which, when electrically powered, magnetically attracts the head portion and thus fixes the latter on the instrument shaft.

According to an advantageous development of the invention, the instrument shaft has, on the side of the second shaped body directed away from the first shaped body, a second cross-sectional reduction which encircles the longitudinal axis of the instrument shaft and at which the cross section of the instrument shaft starting from the second shaped body decreases along the instrument shaft. This has the advantage that, by means of the second shaped body and the second cross-sectional reduction, the instrument shaft can also be fixed at a defined position on the hollow organ via a loop or a tensioning band, the loop or the tensioning band being placed in the area of the second cross-sectional reduction and then being pulled tight.

According to an advantageous development of the invention, the first shaped body has rounded, edgeless transitions to the first cross-sectional reduction. According to an advantageous development of the invention, the second shaped body has rounded, edgeless transitions to the second cross-sectional reduction. In this way, further gentle transitions are present which protect the tissue.

The first and/or second shaped body can be designed to be rotationally symmetrical in the longitudinal direction of the surgical appliance. It is advantageous to provide rounded, edgeless transitions on the first shaped body at the transition to the first or third cross-sectional reduction, and on the second shaped body at the transition to the second or third cross-sectional reduction. In an advantageous embodiment of the invention, the first and/or second shaped body can have the shape of a ball or an olive. In an advantageous embodiment, the first and/or second shaped body is made from an electrically insulating material, e.g. a plastic, such as polyethylene, for example. It is in this way possible to avoid undesired current conduction, e.g. from an electric loop. Generally, the first and/or second shaped body can be designed as a body that is convex with respect to the longitudinal axis of the appliance, in particular with a rounded shape along the longitudinal axis of the appliance.

In an advantageous embodiment, the first, second and/or third cross-sectional reductions can be designed as circumferential grooves with a U-shaped or V-shaped profile.

According to an advantageous development, the counter-pressure plate is secured on the head portion in such a way as to be movable, in particular in relation to the first shaped body, e.g. via a joint or a hinge, and the instrument shaft and/or the grip portion has an actuating mechanism with which the counter-pressure plate can be moved from a first position to a second position by remote control from the instrument shaft or grip portion. This has the advantage that, in the course of the preparation and performance of an anastomosis, the counter-pressure plate can be changed in terms of its position in the organ stump. In particular, provision can be made that, in order to introduce the head portion with the counter-pressure plate into the organ stump and to later remove it after completion of the anastomosis, the counter-pressure plate is brought to a tilted, oblique position, in which it can more easily be introduced into and removed from the organ stump. For the production of a circular stapled suture, the counter-pressure plate can be brought by remote control via the actuating mechanism to a position, e.g. the second position, in which that surface of the counter-pressure plate forming the abutment for the staples during the stapling procedure is arranged approximately perpendicular to the longitudinal axis of the organ stump, such that, for producing the circular stapled suture all the way round, the same distances are obtained between the stapling unit of a circular stapler and the counter-pressure plate. The counter-pressure plate can be brought from the first position to the second position, for example, directly after the insertion of the head portion into the organ stump, when the head portion is positioned at the desired location.

According to an advantageous development of the invention, the counter-pressure plate is pivotable with respect to the longitudinal axis of the surgical appliance or of the head portion, but the first and second shaped bodies are not pivotable with respect to the longitudinal axis. This permits a more secure and more robust construction of the surgical appliance, since only a small part of the appliance has to be designed to be pivotable via a pivot mechanism. In addition, the hollow organ is protected in this way during the operation.

According to an advantageous development of the invention, the head portion has at least one retaining element by which the counter-pressure plate is fixed in its first and/or second position against movements not triggered by the actuating mechanism. For example, the counter-pressure plate can latch in the first position or second position, for which purpose, for example, a catch mechanism actuated by a spring force can be provided. The fixing by the retaining element can be overcome by the actuating mechanism.

According to an advantageous development of the invention, the head portion and the instrument shaft each have a hollow channel. The actuating mechanism has a thread-like element which can be guided from the counter-pressure plate through the hollow channel of the head portion and through the hollow channel of the instrument shaft. This permits a simple configuration of the actuating mechanism. A further advantage is that, after the instrument shaft has been removed from the head portion, the thread-like element remaining on the head portion can be employed for further uses during the preparation and performance of the anastomosis, e.g. as a guide aid for guiding a circular stapler to the head portion remaining in the organ stump.

According to an advantageous development of the invention, the instrument shaft has a hollow channel in which a thread-like pulling element for triggering the releasable coupling is provided and is connected to the releasable coupling.

The aforementioned object is also achieved, as per claim 8, by a surgical resection device designed to separate part of a hollow organ of a human or animal so as to prepare for a circular anastomosis, with a grip area, which is designed to allow the resection device to be held by a user, with an elongate body, which adjoins the grip area and whose distal end area directed away from the grip area has a resection loop, designed to separate part of the hollow organ, and a first ligature loop, wherein the resection loop is arranged nearer to the grip part than the first ligature loop, and wherein the resection loop and the first ligature loop are designed to be guided from the outside of a stump of a hollow organ of a human or animal and over this stump, wherein the first ligature loop and the resection loop can each be contracted by remote control from the grip area or the elongate body. Such a resection device can advantageously be used to separate a portion of the hollow organ at a defined cutting location, wherein the cutting position for the resection loop can be defined and fixed by prior contraction of the ligature loop. A further advantage of the resection device is that a hollow organ can be separated from the outside. The resection loop used can in particular be an electric loop, i.e. a wire which is supplied with electric current and which undergoes considerable heating at least in the area of the loop and in this way thermally separates a part of the hollow organ. The ligature loop serves as a clamping loop, i.e. for clamping this loop on the hollow organ when the ligature loop is contracted. In this way, the surgical resection device is at the same time also fixed at a defined location.

According to an advantageous development of the invention, the resection device has, in the distal end area of the elongate body, a second ligature loop, which is arranged nearer to the grip area than the resection loop, wherein the second ligature loop can be contracted by remote control from the grip area or the elongate body. By means of the second ligature loop, the resection device can be fixed on the hollow organ at a second location, such that, when the resection device is fixed via the first and second ligature loops, it is fixed securely on the hollow organ on both sides of the resection loop, such that the separating procedure can be performed with the resection loop at a defined location. At the same time, the hollow organ is tensioned between the first and second ligature loops, such that it can be more easily separated by the resection loop arranged between these.

According to an advantageous development of the invention, the first ligature loop, the resection loop and, if appropriate, the second ligature loop can be contracted from the grip area by way of pull threads. A separate pulling thread is advantageously provided for each loop. The loops can be easily actuated via the pulling threads, such that the loops are able to be contracted from the direction of the grip area.

According to an advantageous development of the invention, the resection loop is designed to be loose and in particular is not coupled to the first and/or second ligature loop. In particular, all three loops, i.e. the resection loop and the first and second ligature loops, can be designed to be loose and not coupled to one another. This has the advantage that the loops can better adapt to one another and can fit variably into the first, second and third cross-sectional reductions. This facilitates the work of the operator, since less effort is needed to position the loops precisely in relation to the cross-sectional reductions. A further advantage is that the resection loop can be tightened independently of the first and/or second ligature loop. This has advantages as regards the course of the operation. Thus, the first and/or second ligature loop can first of all be drawn tight, such that a suitable positioning of the resection device is already obtained in this way and, at the same time, the organ stumps are safely closed. Only then is the resection loop brought into use. The operator thus has complete control of when each loop is individually tightened.

The aforementioned object is also achieved, as per claim 11, by a kit composed of a surgical appliance of the above-described type and of a surgical resection device of the above-described type. It is advantageous here for the surgical resection device and the surgical appliance to be matched to each other in terms of their spatial dimensions. With said kit, preparation can be made particularly advantageously and effectively for a circular anastomosis, wherein the previously required transverse suture for closing the organ stump can be omitted. This has the advantage that further complications can be avoided, e.g. during the subsequent circular stapling.

According to an advantageous development of the invention, the distance between the emergence points of the first ligature loop and of the resection loop from the elongate body corresponds to the distance between the first cross-sectional reduction on the head portion and the separation plane between the head portion and the instrument shaft. This has the advantage that, during the preparation for an anastomosis, the first ligature loop and the resection loop can each precisely be positioned over, respectively, the first cross-sectional reduction and the separation plane between the head portion and the instrument shaft. The first ligature loop can then be contracted. By doing so, the resection loop is located at a fixed position in the area of the separation plane at which the separation procedure on the hollow organ is then to be performed via the resection loop. In this way, the surgical appliance and the surgical resection device are adapted to each other and can be used with each other with the stated advantages.

According to an advantageous development of the invention, the distance between the emergence points of the resection loop and of the second ligature loop from the elongate body corresponds to the distance between the second cross-sectional reduction on the instrument shaft and the separation plane between the head portion and the instrument shaft. In this way, the surgical appliance and the surgical resection device are also adapted to each other in terms of the second ligature loop and the second cross-sectional reduction. By pulling on the first and second ligature loops, the resection loop is positioned at the desired location between the ligature loops, wherein a certain distance to the ligature loops is maintained.

The first and second shaped bodies of the surgical appliance also serve at the same time as spacers for the resection loop, which is maintained at a defined distance from the first and second ligature loops by the two shaped bodies.

The aforementioned object is also achieved, as per claim 14, by a surgical circular stapler designed for performing a circular anastomosis, with an annular stapling unit designed to eject staples, wherein the stapler has a coupling mechanism which is designed for coupling to a head portion located in a stump of a hollow organ of a human or animal, said head portion being part of a surgical appliance according to one of claims 1 to 7. Advantageously, the stapler has a coupling mechanism compatible with the releasable coupling of the surgical appliance, such that coupling to the head portion of the surgical appliance is possible without any problem. In this way, the stapler is advantageously adapted to the surgical appliance, in particular to the head portion thereof. The coupling mechanism can, for example, latch automatically onto the head portion.

According to an advantageous development of the invention, the coupling mechanism is arranged centrally in the annular stapling unit.

According to an advantageous development of the invention, the stapler has a handgrip which is designed to allow the stapler to be held by a user, wherein the handgrip is provided with a remote-control means which, when activated, actuates the coupling mechanism for coupling the stapler on the head portion of the surgical appliance located on a stump of the hollow organ of a human or animal.

According to an advantageous development of the invention, the stapler has an inner hollow channel for receiving a thread-like element of the head portion, which element is guided from the counter-pressure plate through the hollow channel of the first shaped body, wherein the inner hollow channel of the stapler, at the distal end of the stapler remote from the handgrip, merges into an opening. The thread-like element of the head portion can be inserted into this opening. In this way, the thread-like element, which is part of the actuating mechanism of the counter-pressure plate, can also be used, during and after the performance of the anastomosis, from the direction of the stapler. From the direction of the stapler, and by way of the thread-like element, the counter-pressure plate can be brought to the oblique, tilted position after the stapling procedure has been performed, which simplifies the removal of the head portion from the then stapled organ stump.

According to an advantageous development of the invention, the opening of the inner hollow channel of the stapler is arranged inside the coupling mechanism.

A further advantageous embodiment of the invention concerns a kit composed of a surgical appliance of the above-described type, of a surgical resection device of the above-described type, and of a surgical circular stapler of the above-described type.

The invention is explained in more detail below on the basis of illustrative embodiments and with reference to drawings, in which:

FIGS. 1 and 2 show a surgical appliance according to claim 1, and

Figure 3:
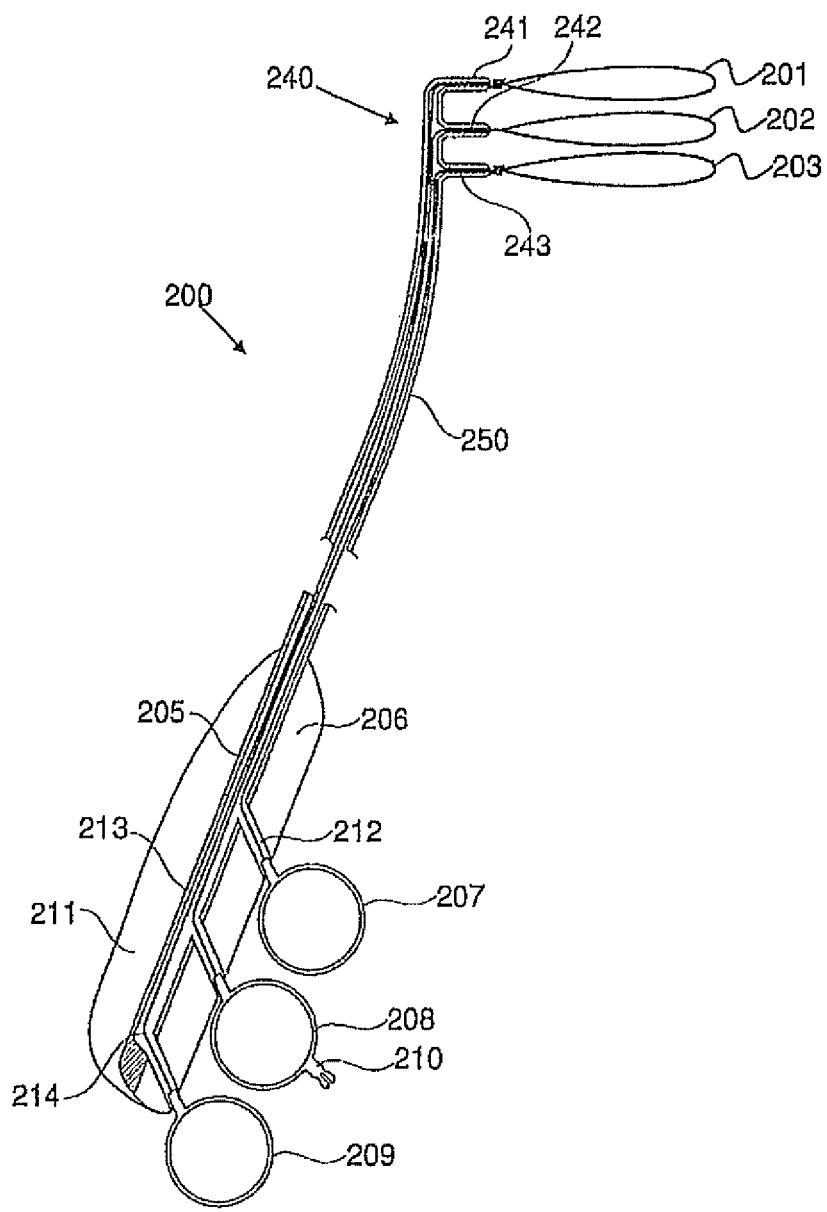
FIG. 3 shows a surgical resection device according to claim 8.
Figure 7:
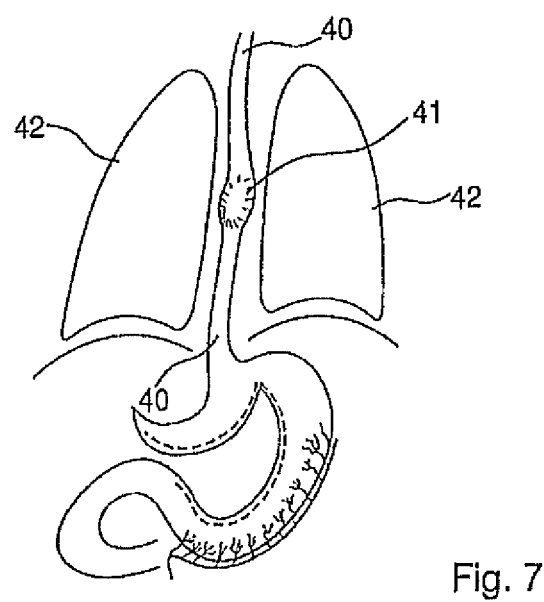
Figure 8:
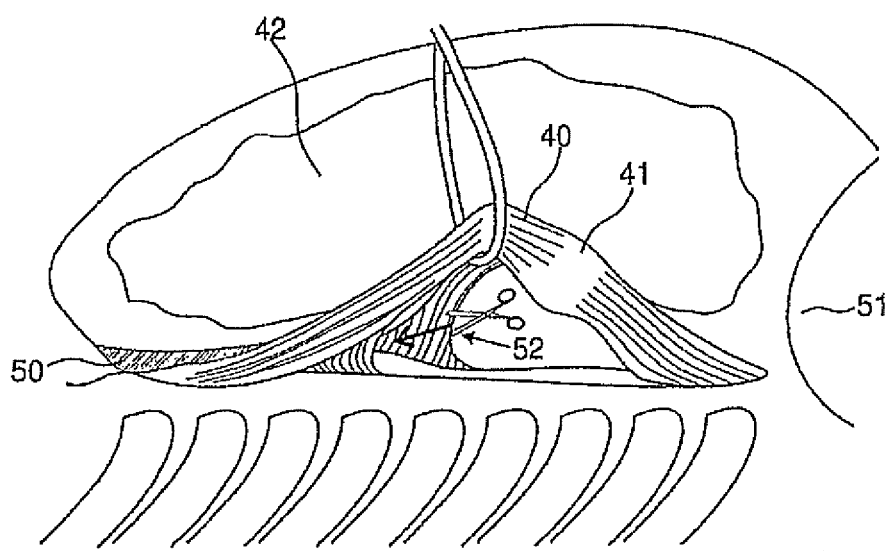
Figure 9:
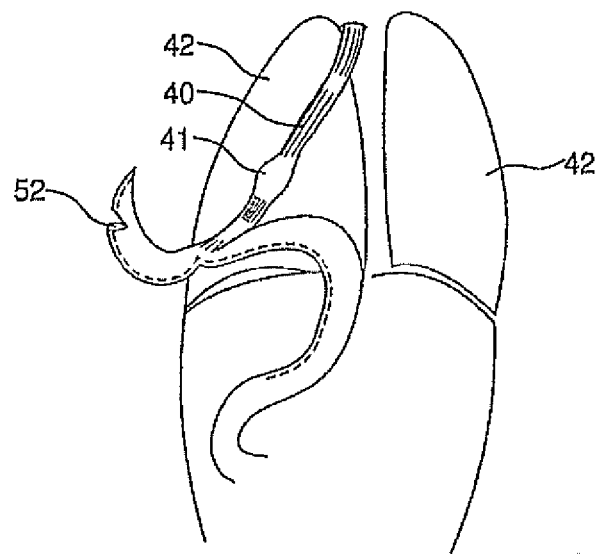
Figure 10:
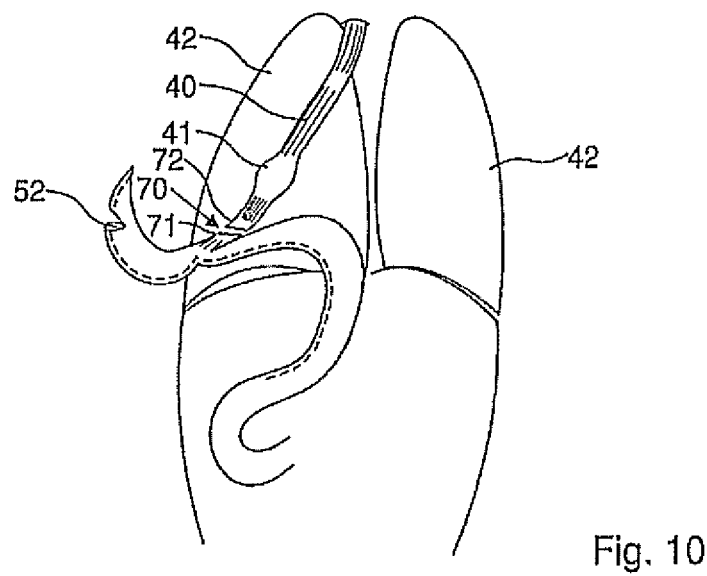
Figure 22:
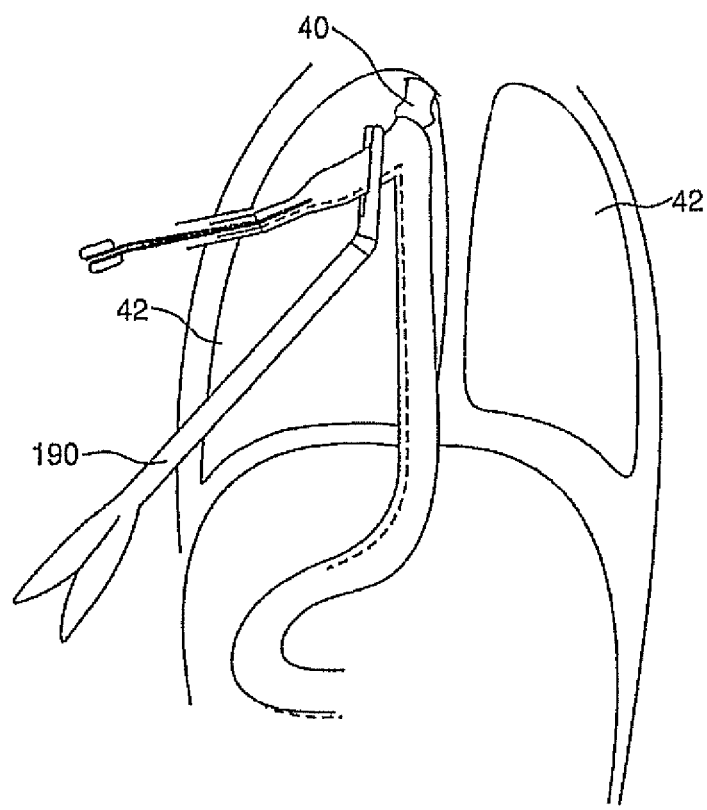
Figure 23:
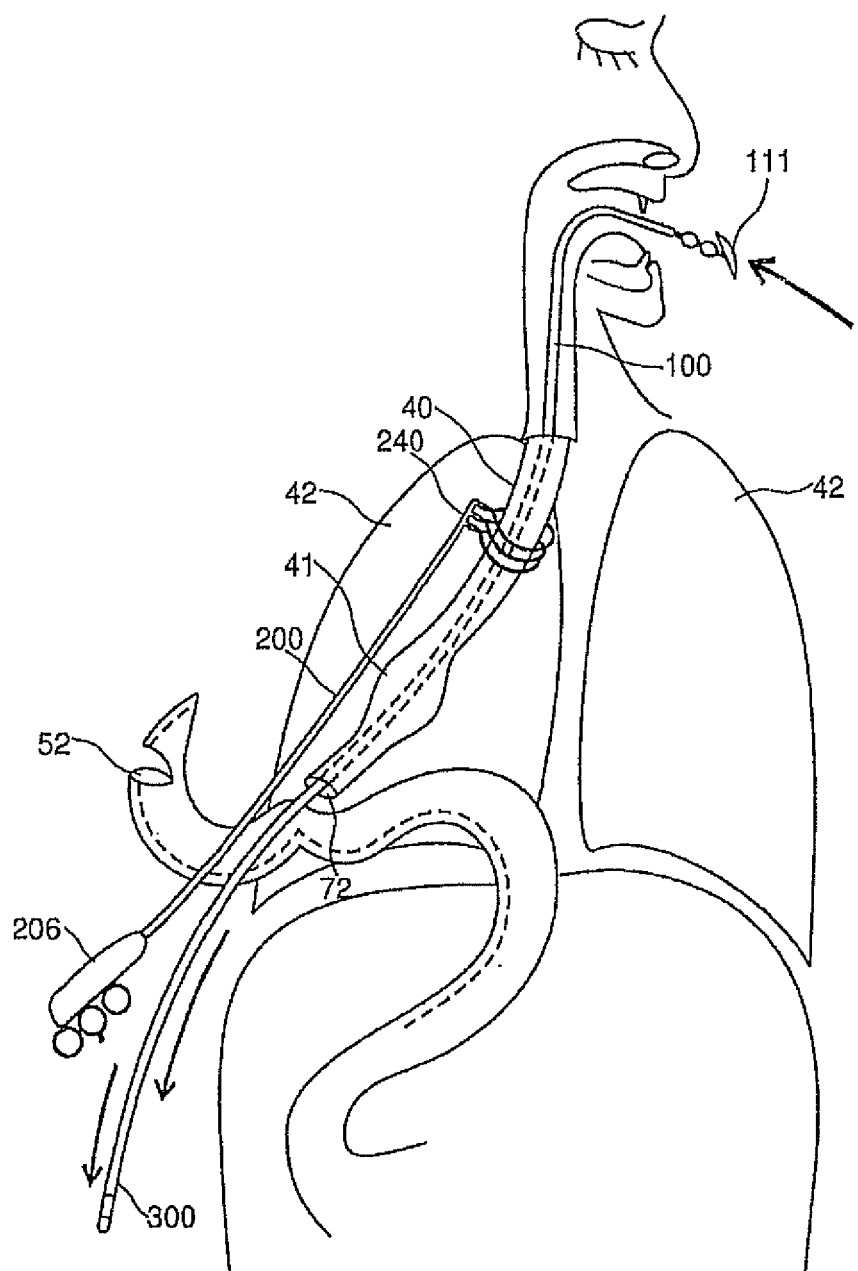
Figure 24:
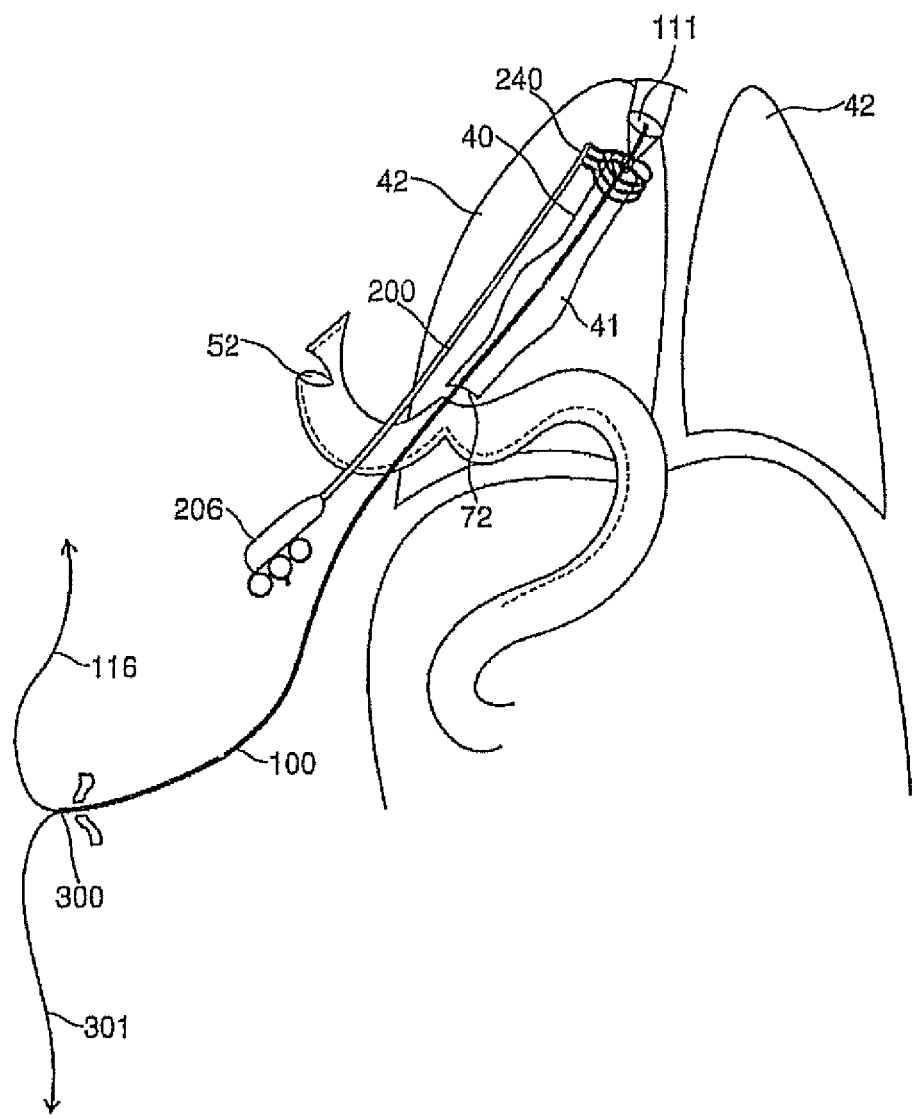
Figure 25:
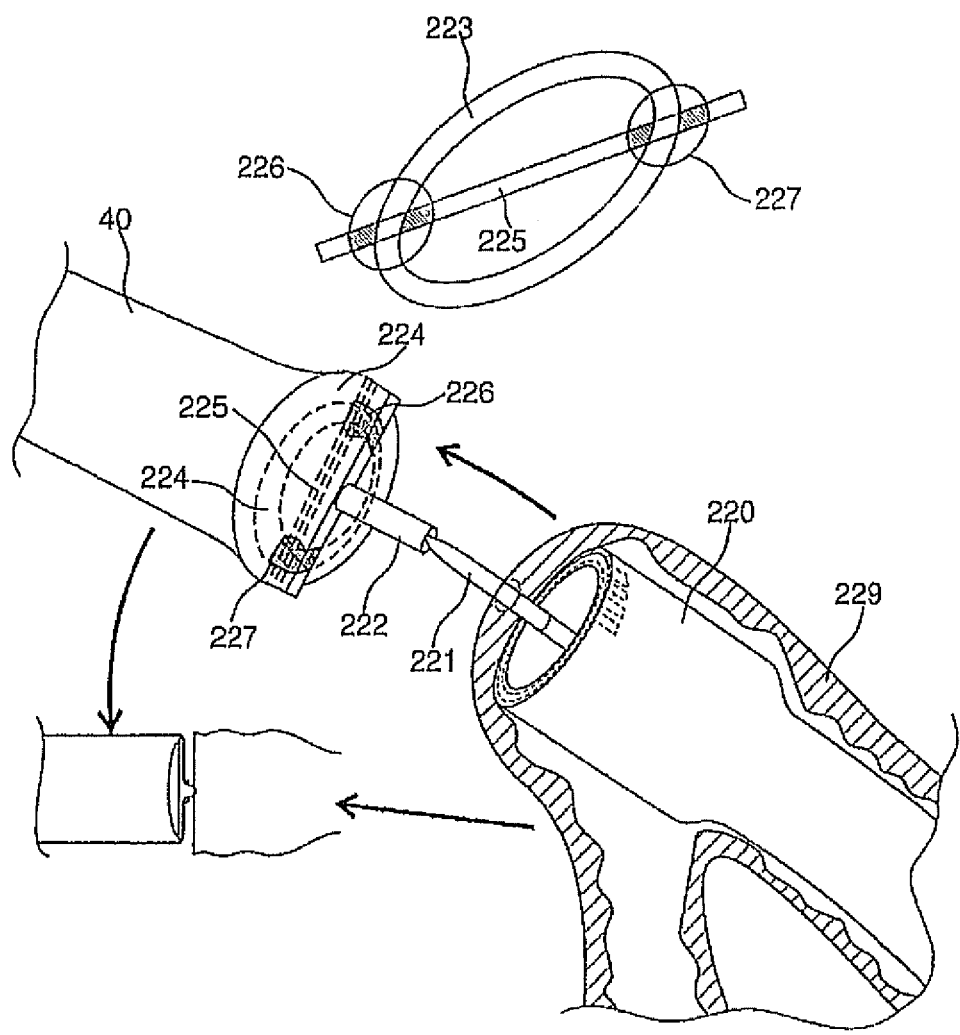
Figure 26:
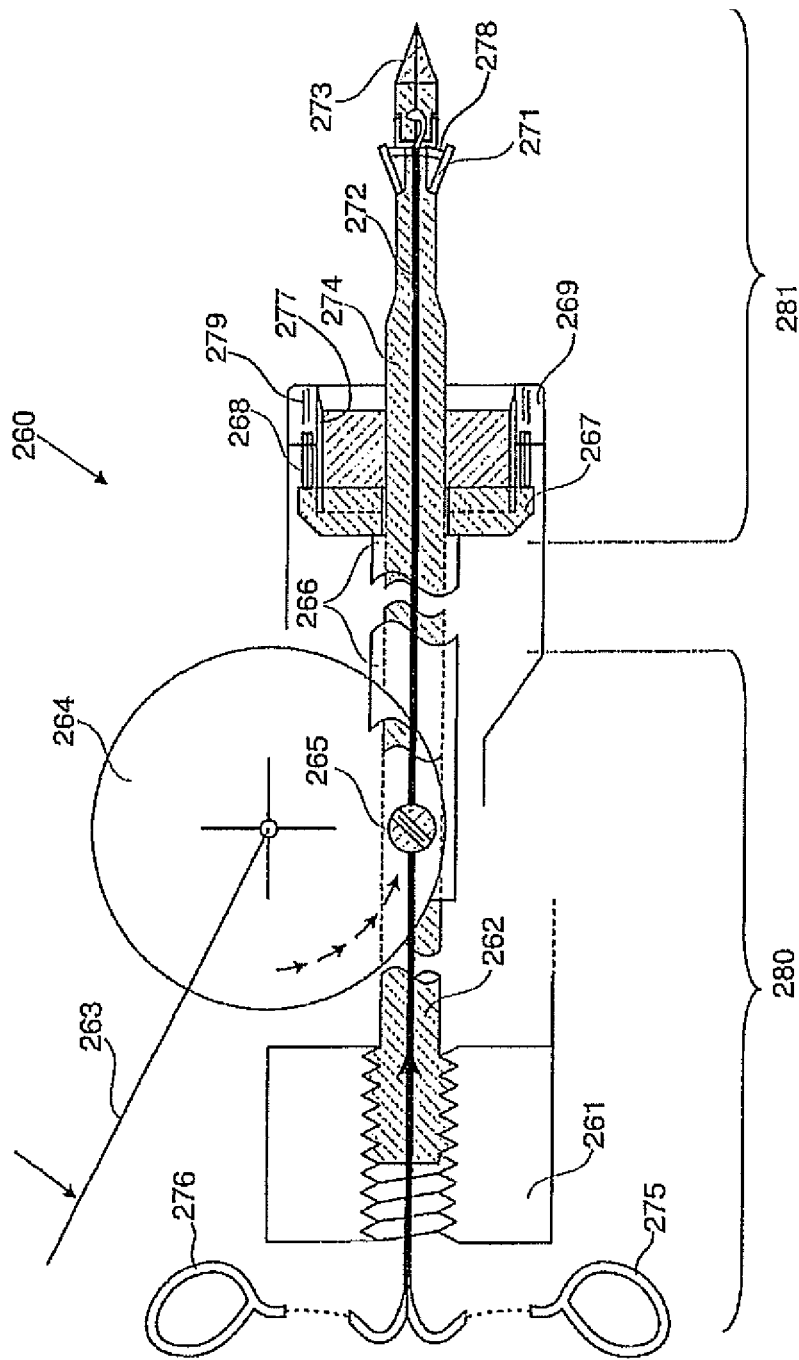

FIGS. 4 to 6 show a further embodiment of a surgical appliance according to claim 1, and FIGS. 7 to 22 show the preparation and performance of an anastomosis using the appliance according to FIG. 1, and FIGS. 23 and 24 show the performance of the steps shown in FIGS. 8 and 9, using an appliance according to FIG. 3, and FIG. 25 shows performance of an anastomosis according to the prior art, and FIG. 26 shows a stapler, and FIGS. 27 to 29 show a further embodiment of a surgical appliance according to claim 1.

In the figures, the same reference signs are used for elements corresponding to each other.

FIG. 1 shows a surgical appliance 100 designed to be introduced into a stump of a hollow organ of a human or animal so as to prepare for a circular anastomosis. The appliance 100 has an instrument shaft 120 in the form of an elongate body which, at a proximal end, has a grip portion 121. The grip portion 121 allows the appliance 100 to be gripped and held by a user. At the distal end remote from the grip portion 121, the instrument shaft 120 has a releasable coupling 113. A head portion 130 of the appliance 100 is coupled to the instrument shaft 120 by means of the releasable coupling 113. The head portion 130 can be released from the instrument shaft 120 by release of the coupling 113. The instrument shaft 120 has a shaft area 105 which is hollow on the inside. A Bowden cable 104 and a pull thread 116 are guided through the shaft area 105. The grip area 121 has a finger-grip part 102, and an actuation ring 101 connected to the Bowden cable 104. The Bowden cable 104 is fixed on the finger-grip part 102 with a Bowden cable seal 103. By moving the finger-grip part 102 relative to the actuation ring 101, the Bowden cable 104 can be actuated. The pull thread 116 ends in the area of the actuation ring 101 in a thread loop 106. The latter is locked by a lock 107.

At the end remote from the grip area 121, the instrument shaft 120 has a second shaped body 108, of which the function will be explained in detail below. In the direction of the grip portion 121, the second shaped body 108 merges into a circumferential second cross-sectional reduction 115, e.g. in the form of a furrow or a groove. On the other side of the second cross-sectional reduction 115, the cross section of the instrument shaft 120 increases again.

The head portion 130 has a first shaped body 109 and a counter-pressure plate 111, e.g. made of metal. The counter-pressure plate 111 is secured on the head portion 130 in an articulated and pivotable manner via a joint 114. The counter-pressure plate 111 is pretensioned by a spring mechanism 110 in the oblique position shown in FIG. 1 and is automatically set to this position by the spring mechanism 110. The pull thread 116 is guided through the head portion 130 as far as the counter-pressure plate 111 and connected to the latter, e.g. via a loop. By pulling on the thread loop 106, a tensile force can be applied to the counter-pressure plate 111, as a result of which the counter-pressure plate 111 can be moved from the position predefined by the spring mechanism 110 to a second position lying approximately perpendicular to the longitudinal axis of the appliance 100, as is shown by broken lines in FIG. 2. The spring mechanism 110 can have a catch, such that the counter-pressure plate 111 latches in the position shown by broken lines in FIG. 2 and is not guided back by spring force.

Between the first shaped body 109 and the counter-pressure plate 111, the head portion 130 narrows to a first cross-sectional reduction 117 which, for example, can be designed like the second cross-sectional reduction 115, but can also have a different shape.

The first and second shaped bodies can, for example, be made of plastic, e.g. of polycarbonate.

By pulling on the finger-grip part 102, the Bowden cable 104 can be actuated, as a result of which the releasable coupling 113 is released. The head portion 130 can then be separated from the instrument shaft 120.

The instrument shaft 120 can, for example, have a length of ca. 45 cm and be designed as a slightly curved tube. It can have a rigid design made of metal or can have an alternative flexible designed made of plastic, e.g. polyethylene with wire reinforcement. The actuation ring 101 is disconnectable from the grip portion 121, such that the actuation ring 101 can be pulled freely and the thread loop 106 can also be released from the actuation ring 101. The head portion 130 can have a length of approximately 25 mm, for example.

FIG. 3 shows a surgical resection device 200 designed to separate part of a hollow organ of a human or animal so as to prepare for a circular anastomosis. The resection device 200 has a grip area 206, which is designed to allow the resection device 200 to be held by a user. The grip area 206 can be shaped ergonomically in the manner of a handle. The grip area 206 is adjoined by an elongate body 250, which can be designed as a tubular shaft. At a distal end area 240 directed away from the grip area 206, there are emergence points 241, 242, 243, which are arranged at an angle with respect to the elongate body 250 and from which there emerge different threads or wires that are guided through the elongate body 250 from the grip portion 206 and that are formed into loops 201, 202, 203 outside the emergence points 241, 242, 243. A first ligature loop 201 is provided at a first emergence point 241. A resection loop 202 is provided at a second emergence point 242. A second ligature loop 203 is provided at a third emergence point 243. The first ligature loop 201 is here connected, by a first pull thread 212, to a first pull ring 207 arranged on the grip portion 206. The second ligature loop 203 is connected, by a second pull thread 214, to a second pull ring 209 arranged on the grip portion 206. The resection loop 202, which can be designed as an electrical loop for example, is connected by an electrically conductive wire 213 to a third pull ring 208 arranged on the grip portion 206. The third pull ring 208 has an electrical connection 210, e.g. in the form of a plug connector, for connection to a source of electrical power.

The resection loop 202 can be supplied with electric current via the wire 213 and can thus be heated. In this way, a thermal separation of parts of a hollow organ can be carried out. The wire 213 can also be designed as a braided wire.

The loops 201, 202, 203 can be contracted by pulling on one of the respective pull rings 207, 208, 209, as will be explained in more detail below in connection with the use of the resection device 200.

The distance between the emergence points 241, 242, 243 can, for example, measure ca. 10 to 12 mm in each case. The length of the emergence points 241, 242, 243, i.e. of the angled extensions, can be in the range of ca. 12 to 15 mm, for example. By using a special knot, or by means of some other fixing mechanism, e.g. a return stop in the manner of a cable binder, the ligature loops 201, 203 and the resection loop 202 can be protected from opening again after being contracted.

The source of electric power can be designed as a standard coagulation transformer, for example. A monopolar current for cutting tissue is applied via the resection loop 202.

With reference to FIGS. 1 and 2, a first embodiment of the surgical appliance 100 was explained which is provided for so-called retrograde introduction of the counter-pressure plate via the distally opened esophagus.

With reference to FIGS. 4 to 6, a second embodiment of the surgical appliance 100 is described which serves for antegrade introduction of the counter-pressure plate, i.e. oral introduction, which is necessary, for example, if retrograde advance of the counter-pressure plate via the distally opened esophagus is not possible on account of a tumor, for example. The antegrade configuration of the surgical appliance 100 differs from the appliance 100 shown in FIGS. 1 and 2 only in terms of the length of the instrument shaft 120 and the design of the grip portion 121. The instrument shaft 120 per se and the head portion 130 are otherwise unchanged. In each of FIGS. 4 to 6, the antegrade version 300 of the grip portion is shown, specifically in different stages of use. FIG. 4 shows the grip portion 300 in a preparation phase prior to oral introduction of the appliance 100. This figure once again shows the pull thread 116 with the thread loop 106. Instead of the Bowden cable 4, a second pull thread 301 with a thread loop 302 is provided. The second pull thread 301 here serves, instead of the Bowden cable 4, to actuate the releasable coupling 113. The pull thread 116 has the same function as explained in relation to FIG. 1. In addition, a securing thread 303 is provided, via which the thread loops 106, 302 can be fixed on the grip portion 300, as is shown in FIGS. 5 and 6. For covering, an envelope 304, e.g. a piece of adhesive tape, can be fitted in the corresponding area of the grip portion 300.

In the antegrade version of the appliance 100, the latter is introduced, with the grip portion 300 to the front, into the patient's mouth and then emerges from the distally opened esophagus. The grip portion 300, which emerges first, is then seized by the user and pulled further, until the counter-pressure plate 111 is guided to the desired location in the hollow organ. The envelope 304 can then be removed, the securing thread 303 can be released, and the releasable coupling 113 can be actuated via the second pull thread 301, such that the instrument shaft 120 can be removed from the head portion 130.

In the antegrade version of the appliance 100, the instrument shaft 120 can have a length of about 100 cm, for example.

After removal of the instrument shaft 120, the head portion 130 remains in the esophagus or in the respective hollow organ. The pull thread 116 can also remain there, in which case the thread loop 106 is optionally separated. The pull thread 116 can then be used as a guide aid for the subsequent steps of the anastomosis, as is explained below.

The use of the above-described surgical appliances 100, of the surgical resection device and of a surgical circular stapler in the preparation and performance of an anastomosis is described below.

FIG. 7 shows, as hollow organ, the stomach tube and the esophagus 40 of a patient. It is assumed that the esophagus 40 has a tumor 41. For illustrative purposes, the lungs 42 are also shown. Laparoscopic shaping of the stomach tube is now performed by incomplete closure of the lesser curvature. After the patient has been moved to a left lateral position, thoracoscopic esophagectomy is performed from the diaphragmatic opening to above the tumor 41. As is shown in FIG. 8, a minithoracotomy is performed in the area of the tracer access and the distal lobe of the lesser curvature is guided out, the lobe optionally being opened to aspirate the esophagus and stomach. FIG. 8 shows this in a view from the right. The lung 42, the trachea 50, the esophagus 40, the tumor 41, the diaphragm 51 can be seen, and also the site 52 where an incision is made.

FIG. 9 in turn shows the esophagus 40, the tumor 41, the lungs 42 and the incised surface 52. According to FIG. 10, the esophagus 40 is separated at a site 70. In an area 71 of the cardia, closure of the esophagus is performed with a linear endostapler. The other opened end 72 can likewise be closed with a linear endostapler.

Figure 11:
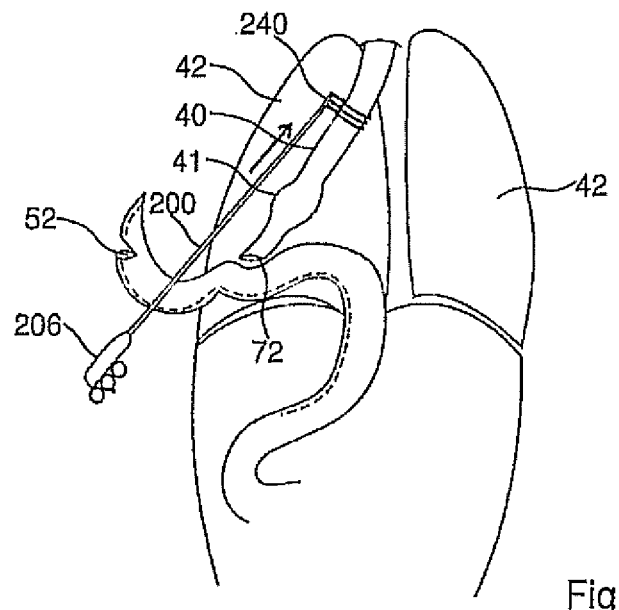
Figure 12:
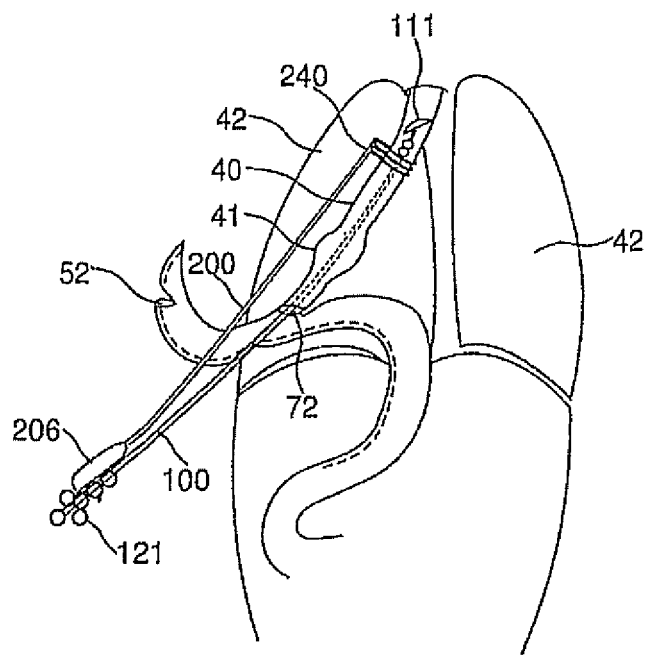

As is shown in FIG. 11, the closed esophagus 40 is gripped, and the loops 201, 202, 203 of the resection device 200 according to FIG. 2 are guided over the esophagus and positioned above the tumor 41. Then, as is shown in FIG. 12, a surgical appliance 100 according to FIG. 1 is guided, with the head portion 130 to the front, through the opened end 72 into the esophagus 40. The counter-pressure plate 111 is advanced proximally of the tumor 41 to about the level of the loops 201, 202, 203. Beforehand, the stapled suture at the opened end 72 was opened again.

Figure 13:
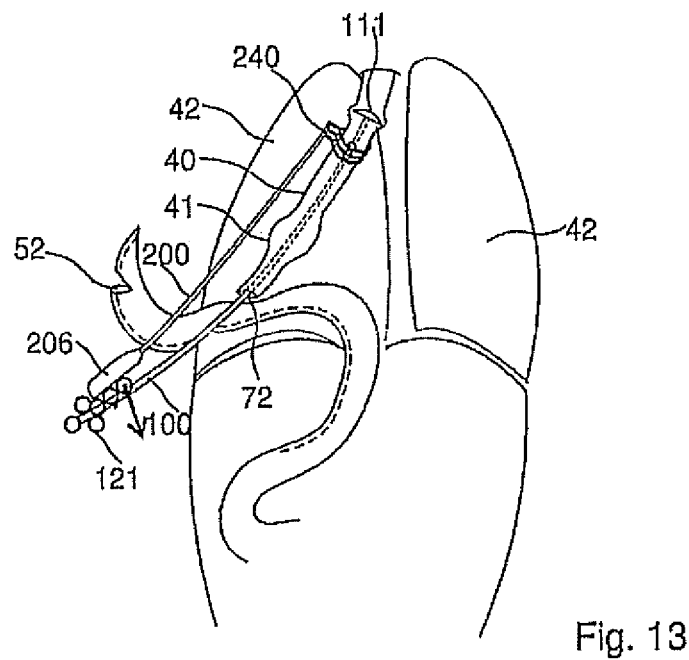
Figure 14:
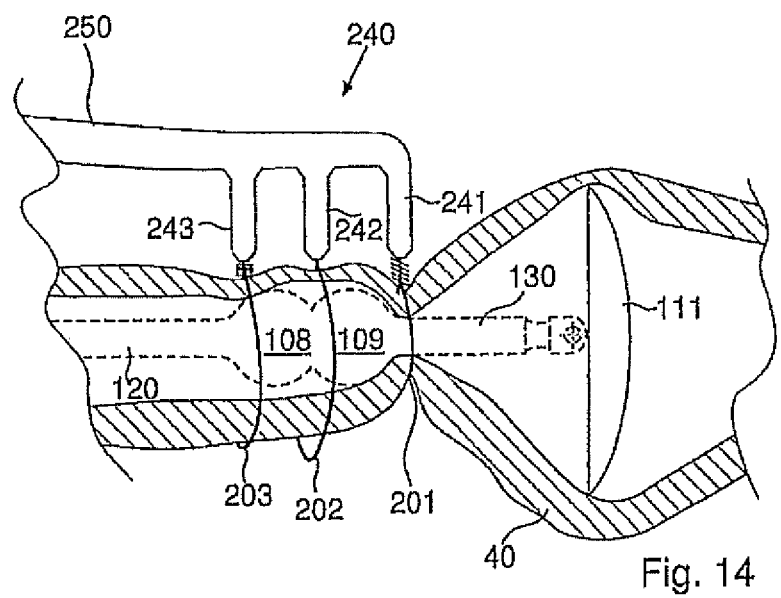
Figure 15:
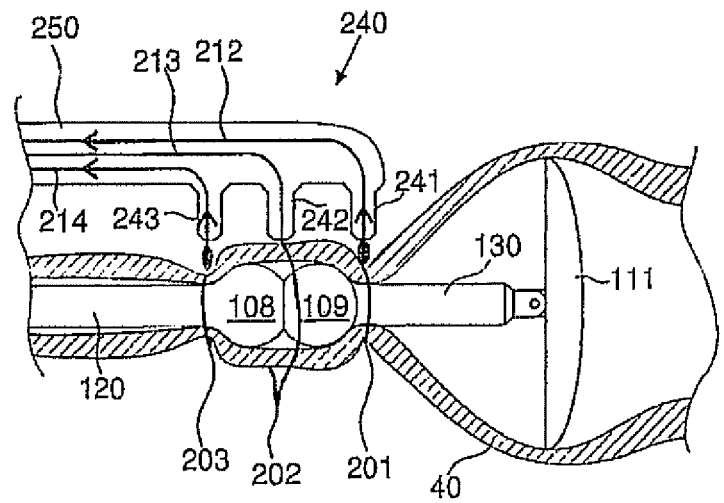
Figure 16:
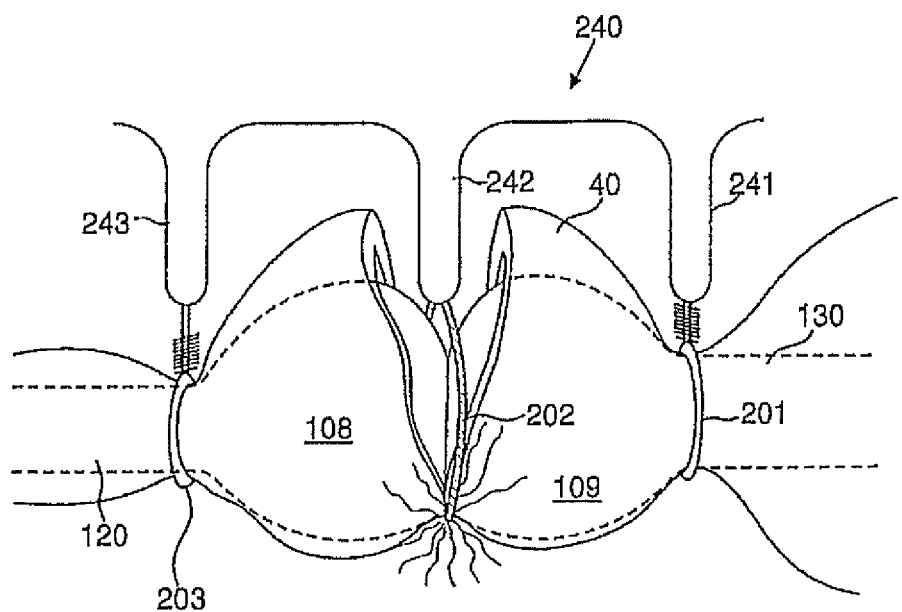

According to FIG. 13, the thread loop 106 of the appliance 100 is pulled, as a result of which the counter-pressure plate 111 is straightened from the oblique position. In addition, by pulling on the pull ring 207 of the resection device 200, the first ligature loop 201 is drawn tight, as is also depicted in an enlarged detailed view in FIG. 14. In this way, the head portion 130 of the surgical appliance 100 is fixed in the stump of the esophagus 40. In addition, the resection device 200 is fixed and adjusted in relation to the head portion 130. The second ligature loop 203 is then also pulled tight, as is shown in FIG. 15. The ligature loops 201, 203 slip over the first and second shaped bodies 8, 9 into the respectively desired position in the cross-sectional reductions 115, 117 and thus tension the esophagus 40 in the area lying between them. The resection loop 202 is then pulled tight and supplied with current. As a result of current being supplied to the resection loop 202, the esophagus is severed between the two ligature loops 201, 203, as is shown in FIG. 16.

Figure 17:
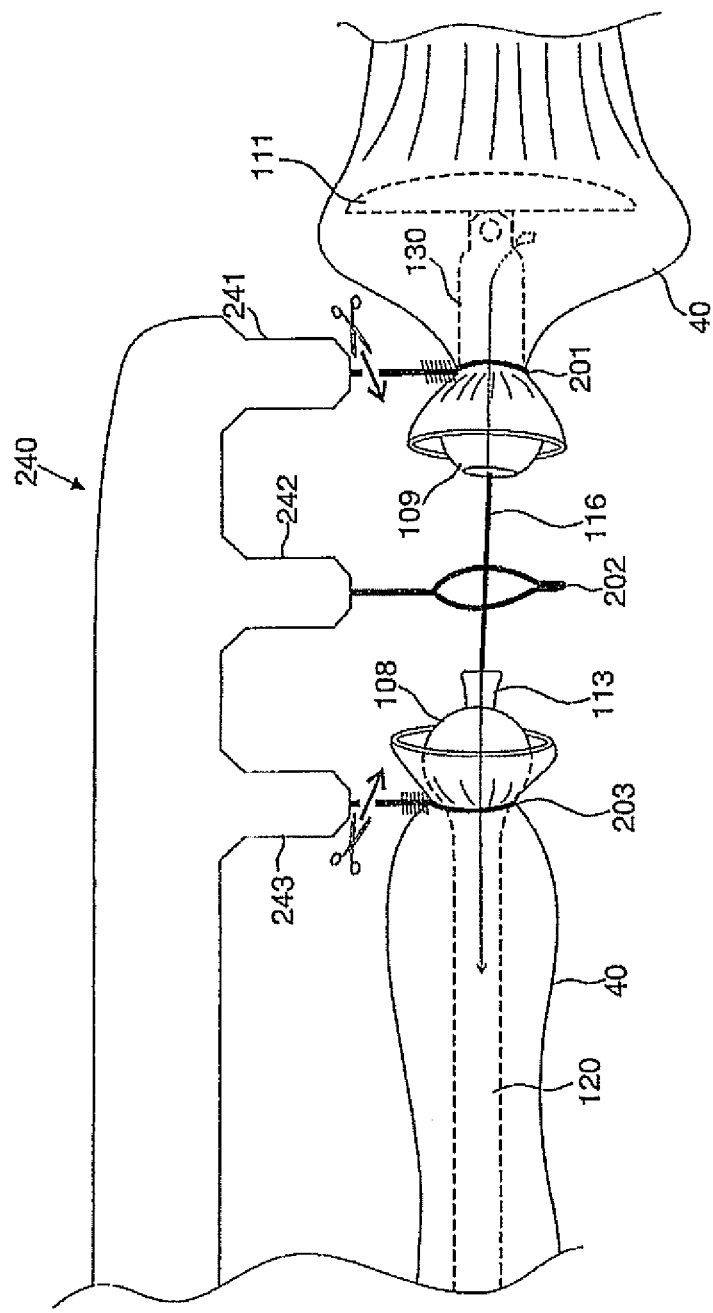
Figure 18:
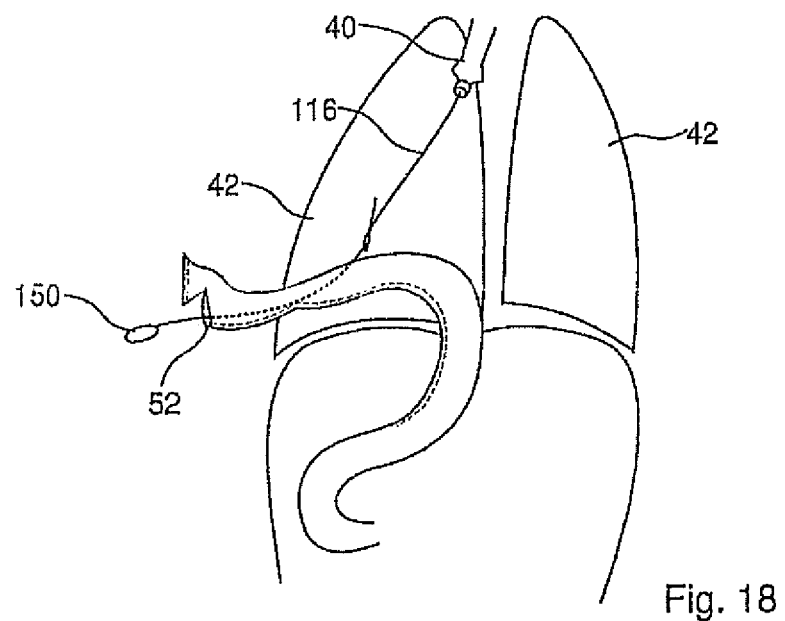
Figure 19:
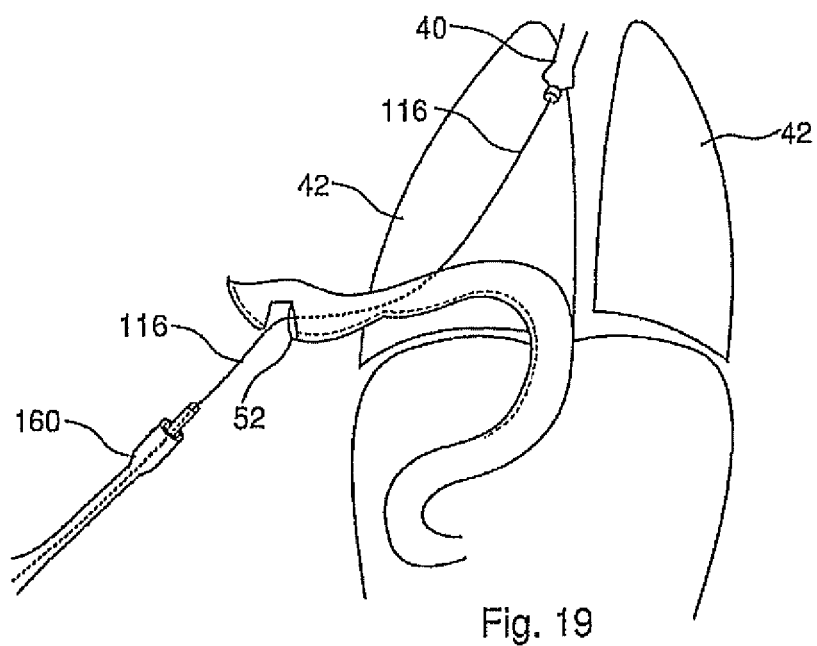

FIG. 17 shows the severed esophagus. After this, the ligature loops 201, 203 are separated from the resection device 200. In addition, by pulling on the finger-grip part 102 of the appliance 100, the releasable coupling 113 is brought to the release position, such that the head portion 130 of the appliance 100 can be separated from the instrument shaft 120. The separated part of the esophagus can then be pulled off by the pull thread 116 after removal from the thorax. As is shown in FIG. 18, the pull thread 116 still present thereafter can then be seized by piercing the stomach tube with a thread catcher 150 and can then be pulled out through the stomach tube via the opening 52. As is shown in FIG. 19, the pull thread 116 can then be guided through a hollow channel of a circular stapler 160. This has the advantage that the stapler 160, with the aid of the pull thread 116, can be easily guided to the head portion 130, which is still located in the stump of the esophagus 40.

Figure 20:
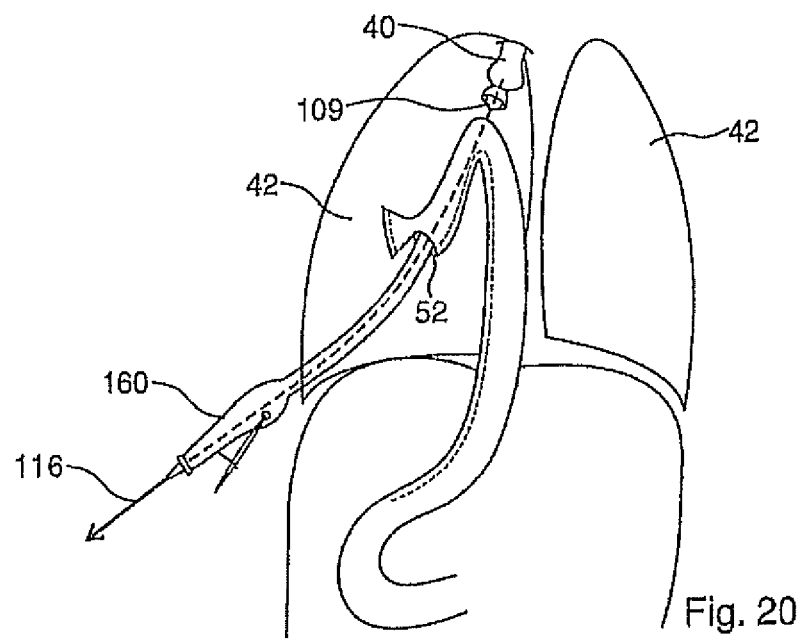
Figure 21:
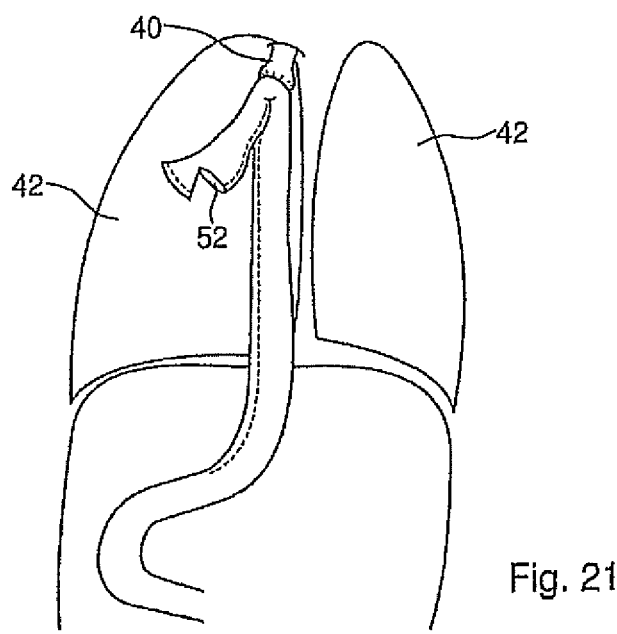

As is shown in FIG. 20, the stomach tube can then be guided on the pull thread 116 to the head portion 130. The circular stapler 116 can then be coupled to the head portion 130 via a coupling mechanism, which is designed similarly to the coupling mechanism 113. A circular stapled suture is then produced in a known manner, with the counter-pressure plate 111 serving as an abutment during stapling. FIG. 21 shows the completion of the anastomosis, the circular stapler having already been removed together with the head portion 130 of the surgical appliance 100.

As is shown in FIG. 22, the rump of the stomach tube is then closed with a linear endostapler 190.

FIG. 23 shows the corresponding procedure when using the antegrade version of the surgical appliance 100, i.e. with the alternative grip portion 300. The grip portion 300 is introduced orally in the lead position.

After the grip portion 300 appears at the distally opened esophagus, it is seized and pulled until the counter-pressure plate 111 is located at the desired position. The already positioned resection device 200 can then be used in the manner described above. FIG. 24 shows the pull thread 116 and the actuating thread 301 after removal of the envelope 304 from the grip portion 300.

FIG. 25 shows the critical zones of the stapled-suture intersections in the procedure according to the prior art. It shows a circular stapler 220 with a coupling tip 221, which serves for introduction into a corresponding coupling sleeve 222 of a counter-pressure plate 224. Here, the stapler 220 is located in the stomach tube 229. Since a linear stapled suture 225 has already been produced in the prior art, the production of a circular stapled suture 223 creates intersection points 226, 227, which can lead to complications. This is advantageously avoided by the present invention.

FIG. 26 shows a surgical circular stapler 260, which is designed to be coupled to a head portion 130 of the surgical appliance 100 described with reference to FIGS. 1 to 6. The stapler 260 can be used, for example, like the stapler 160 shown in FIG. 19. The stapler 260 has a control area 280 with various control elements, and also an operation area 281 arranged at a distance from the control area via an elongate instrument shaft. FIG. 26 principally shows the control area 280 and the operation area 281, while the instrument shaft lying between them is shown in a shortened form. The stapler 260 can in particular have a length of ca. 600 to 700 mm.

In the operation area, the stapler 260 has an annular stapling unit 268, 269 which is designed to eject staples 279. A supply of staples is located in a staple magazine 269. The stapling unit 268, 269 is also provided with a circular scalpel 277, which is connected to a puncher 267. With the circular scalpel 277, an annular section can be cut from the hollow organ. For actuation of the stapling unit 268, 269 and of the circular scalpel 277, the operation area 281 is connected via a hollow puncher push-rod 266 to a staple actuation unit in the control area 280, which unit has a lever 263, and a wheel 264 connected to the lever 263 for joint rotation. By way of the wheel 264, a force applied to the lever 263 is transferred to a fixing screw 265 and thus to the puncher push-rod 266. In this way, the circular staple 277 is first of all driven out and, finally, the stapling unit 268, 269 is actuated to eject staples 279.

In the operation area 281, an inner push-rod 274 is guided centrally through the stapling unit 268, 269 and continues through and beyond the stapling unit from the control area 280. At the end remote from the control area 280, the inner push-rod 274 has a coupling mechanism 271, which is designed corresponding to the coupling mechanism 113 of the surgical appliance 100. In this way, the stapler 260 is designed to be coupled to a head portion 130 of the surgical appliance 100. The coupling mechanism 271 can have two coupling blades, which can be spread open by a spring force and which can be drawn together from the direction of the control area 280 by a pull thread 278. The pull thread 278 is guided through an inner hollow channel of the inner push-rod 274, which extends through the control area 280 as far as a portion 262. There, the pull thread 278 emerges from the control area 280 and ends in a thread eyelet 275. By pulling on the thread eyelet 275, the coupling mechanism 271 can thus be actuated from the direction of the control area 280.

In the operation area 281, the stapler 260 has, in front of the coupling mechanism 271, a removable tip 273 which, upon introduction of the stapler into the hollow organ, serves to puncture the wall of the hollow organ. The tip 273 is connected to a pull thread 272. When the tip 273 is taken off, the pull thread 272, which is likewise guided through the inner hollow channel of the inner push-rod 274, is exposed. The pull thread 272 can be removed from the tip 273 and can be knotted with the pull thread 116 of the head portion 130. By way of a thread loop 276 connected to the pull thread 272, the knotted pull thread 116 can then be pulled through the stapler 260, which permits safe targeting of the stapler 160 to the head portion 130.

The inner push-rod 274 extends into an area 262 in the control area 280. There, the inner push-rod 262, 272 is provided with an outer thread and is arranged inside a rotary knob 261 with a matching inner thread. By turning the rotary knob 261, the inner push-rod 262, 272 in the operation area 281 can be driven out or driven in. The inner push-rod 262, 272 thus moves relative to the outer push-rod 266.

The inner push-rod 262, 272 is arranged inside the outer push-rod 266.

A further embodiment of the surgical appliance 100 is shown in FIGS. 27 to 29. Only the area of the surgical appliance 100 toward the head portion is shown in each of FIGS. 27 to 29, i.e. only part of the instrument shaft is shown, in particular without the grip portion. According to one of the other embodiments of the surgical appliance, the instrument shaft and the grip portion can be designed as explained above.

FIG. 27 shows the part of the surgical appliance 100 toward the head portion, in a view in which concealed internal components are indicated by broken lines. FIGS. 28 and 29 show the area of the surgical appliance 100 according to FIG. 27 in a sectional view in a plane A-A. FIG. 28 shows this in a side view, while FIG. 29 shows it in an isometric view.

The surgical appliance 100 according to FIGS. 27 to 29 again has a first shaped body 109 and a second shaped body 108 which, as illustrated, are completely rounded without sharp edges or corners. Smooth transitions are thereby created. The shaped bodies 108, 109 are combined to form a single component, namely the shaped-body part 270, which in particular can be made in one piece, e.g. milled from a blank or produced by injection molding. The shaped-body part 270 is part of the instrument shaft 120 and is thus secured on the shaft area 105. A releasable coupling mechanism 113 is arranged in a hollow space formed in the shaped-body part 270. In contrast to the illustrative embodiments described above, the head portion 130 does not in this case comprise the first shaped body 109 and can be detached by release of the releasable coupling 113. This has in particular the advantage that the head portion 130 released from the instrument shaft 120 permits better accessibility for the stapler to the counter-pressure plate 111, since the first shaped body 109 is then not in the way. This in turn has the advantage that the first shaped body 109 can be configured independently of the requirements of the stapling procedure, particularly in terms of shape and diameter.

It will be noted that, in the assembled state in the embodiment according to FIGS. 27 to 29, the head portion 130 and the instrument shaft 120 are thus arranged overlapping over a certain area.

The design of the releasable coupling 113 can be seen particularly clearly in the sectional views in FIGS. 28 and 29. As these make clear, the instrument shaft 120, in the direction toward the head portion 130, merges into a pin-like continuation 280, which can be designed similarly to a connector pin in electrical plug connections. The pin-like continuation 280 is inserted into a hollow, bush-like continuation 281 of the head portion 130 and is held therein by friction, by a spring action between the pin-like continuation 280 and the bush-like continuation 281, or by a locking mechanism between them, e.g. in the form of a catch. As will be seen, the head portion 130 is in this way relatively smooth on the other side of the counter-pressure plate 111 and designed without protruding parts. This advantageously permits simple coupling of a surgical circular stapler 260 for producing the circular stapled suture.

The first and second shaped bodies 108, 109 can also be designed in one piece as a common component and be connected rigidly to the instrument shaft 120. Centrally, and oriented in the longitudinal axis, this component 108, 109 has a tubular channel 284, into which, in the axial center thereof, a longitudinally oriented prong 280 in turn protrudes. This prong serves for coupling the head portion 130, wherein the coupling can be effected, for example, by a combination of rotationally symmetrical folds on the prong 282 and a corresponding shaping of the sleeve of the head portion 130 as elongate spring plates 283 which, at the ends, engage in the folds on the prong 282. Release and also coupling of the head portion 130 could be obtained by overcoming the spring resistance of the spring plates 283.

The invention claimed is:

1. A surgical appliance without a stapling unit for generating a surgical stapled suture which is configured to be held by a user for use in a circular anastomosis for connection of two separated hollow organs of a human or animal, comprising:
   an instrument shaft having a grip portion and a head portion;
   a releasable coupling which couples or is used to couple the head portion to the instrument shaft at an end of the instrument shaft remote from the grip portion;
   at least one counter-pressure plate configured to cooperate with of a surgical circular stapler, wherein the at least one counter-pressure plate is associated with the head portion on the instrument shaft;
   a first shaped body and a second shaped body adjacent to the first shaped body, wherein both the first shaped body and the second shaped body have substantially the same size and shape and are located between the grip portion on the instrument shaft and the at least one counter-pressure plate and wherein the first shaped body and the second shaped body extend laterally from the instrument shaft; and
   a central cross-sectional reduction configured for use as a cutting aid for severing a part of the hollow organ, wherein the central cross-sectional reduction encircles the longitudinal axis of the appliance and is located between the first shaped body and the second shaped body, wherein at the location of the central cross-sectional reduction, the cross section of the appliance is reduced in relation to a cross section of the first shaped body and a cross section of the second shaped body, wherein the first shaped body and the second shaped body have rounded transitions without edges where the first shaped body and the second shaped body adjoin the central cross-sectional reduction,
   wherein the first shaped body is part of the head portion and is connected to or formed in one piece with the head portion even in the state when the head portion is uncoupled from the instrument shaft.

2. The surgical appliance as claimed in claim 1, wherein the first shaped body and second shaped body are formed in one piece as a common component.

3. The surgical appliance as claimed in claim 1, wherein the instrument shaft and/or the grip portion has a release mechanism whose actuation allows the releasable coupling to be released by remote control from the instrument shaft or grip portion, such that the instrument shaft can be removed from the head portion.

4. The surgical appliance as claimed in claim 1, wherein the first shaped body is designed for suture-free closure of the stump of the hollow organ, wherein the head portion has, between the first shaped body and the counter-pressure plate, a first cross-sectional reduction which encircles a longitudinal axis of the head portion and at which the cross section of the head portion decreases starting from the first shaped body in the direction of the counter-pressure plate, wherein the counter-pressure plate in turn has a greater cross section than the area of the first cross-sectional reduction, and wherein the length of the first shaped body in the direction of the longitudinal axis of the head portion is greater than the length of the first cross-sectional reduction in the same direction.

5. The surgical appliance as claimed in claim 4, wherein the first shaped body has a rounded, edgeless transitions to the first cross-sectional reduction.

6. The surgical appliance as claimed in claim 1, wherein the instrument shaft has, on the side of the second shaped body directed away from the first shaped body, a second cross-sectional reduction which encircles the longitudinal axis of the instrument shaft and at which the cross section of the instrument shaft starting from the second shaped body decreases along the instrument shaft.

7. The surgical appliance as claimed in claim 6, wherein the second shaped body has a rounded, edgeless transitions to the second cross-sectional reduction.

8. The surgical appliance as claimed in claim 1, wherein the counter-pressure plate is secured on the head portion in such a way as to be movable in relation to the first shaped body, and the instrument shaft and/or the grip portion has an actuating mechanism with which the counter-pressure plate can be moved from a first position to a second position by remote control from the instrument shaft or grip portion.

9. The surgical appliance as claimed in claim 8, wherein the head portion has at least one retaining element by which the counter-pressure plate is fixed in its first and/or second position against movements not triggered by the actuating mechanism.

10. The surgical appliance as claimed in claim 8, wherein the head portion and the instrument shaft each have a hollow channel, and the actuating mechanism has a thread-like element which can be guided from the counter-pressure plate through the hollow channel of the head portion and through the hollow channel of the instrument shaft.

11. A surgical appliance without a stapling unit for generating a surgical stapled suture which is configured to be held by a user for use in a circular anastomosis for connection of two separated hollow organs of a human or animal, comprising:
- an instrument shaft having a grip portion and a head portion;
- a releasable coupling which couples or is used to couple the head portion to the instrument shaft at an end of the instrument shaft remote from the grip portion;
- at least one counter-pressure plate configured to cooperate with of a surgical circular stapler, wherein the at least one counter-pressure plate is associated with the head portion on the instrument shaft;
- a first shaped body and a second shaped body adjacent to the first shaped body, wherein both the first shaped body and the second shaped body are located between the grip portion on the instrument shaft and the at least one counter-pressure plate and wherein the first shaped body and the second shaped body extend laterally from the instrument shaft, wherein the first shaped body is part of the instrument shaft and is connected to or formed in one piece with the instrument shaft, even in the state when the head portion is uncoupled from the instrument shaft; and
- a central cross-sectional reduction configured for use as a cutting aid for severing a part of the hollow organ, wherein the central cross-sectional reduction encircles the longitudinal axis of the appliance and is located between the first shaped body and the second shaped body, wherein at the location of the central cross-sectional reduction, the cross section of the appliance is reduced in relation to a cross section of the first shaped body and a cross section of the second shaped body, wherein the first shaped body and the second shaped body have rounded transitions without edges where the first shaped body and the second shaped body adjoin the central cross-sectional reduction.

12. The surgical appliance as claimed in claim 11, wherein the first shaped body and second shaped body are formed in one piece as a common component.

13. The surgical appliance as claimed in claim 11, wherein the first shaped body is designed for suture-free closure of the stump of the hollow organ, wherein the head portion has, between the first shaped body and the counter-pressure plate, a first cross-sectional reduction which encircles a longitudinal axis of the head portion and at which the cross section of the head portion decreases starting from the first shaped body in the direction of the counter-pressure plate, wherein the counter-pressure plate in turn has a greater cross section than the area of the first cross-sectional reduction, and wherein the length of the first shaped body in the direction of the longitudinal axis of the head portion is greater than the length of the first cross-sectional reduction in the same direction.

14. The surgical appliance as claimed in claim 11, wherein the instrument shaft and/or the grip portion has a release mechanism whose actuation allows the releasable coupling to be released by remote control from the instrument shaft or grip portion, such that the instrument shaft can be removed from the head portion.

15. The surgical appliance as claimed in claim 11, wherein the counter-pressure plate is secured on the head portion in such a way as to be movable in relation to the first shaped body, and the instrument shaft and/or the grip portion has an actuating mechanism with which the counter-pressure plate can be moved from a first position to a second position by remote control from the instrument shaft or grip portion.

16. The surgical appliance as claimed in claim 15, wherein the head portion has at least one retaining element by which the counter-pressure plate is fixed in its first and/or second position against movements not triggered by the actuating mechanism.

17. The surgical appliance as claimed in claim 15, wherein the head portion and the instrument shaft each have a hollow channel, and the actuating mechanism has a thread-like element which can be guided from the counter-pressure plate through the hollow channel of the head portion and through the hollow channel of the instrument shaft.

18. The surgical appliance as claimed in claim 11, wherein the instrument shaft has, on the side of the second shaped body directed away from the first shaped body, a second cross-sectional reduction which encircles the longitudinal axis of the instrument shaft and at which the cross section of the instrument shaft starting from the second shaped body decreases along the instrument shaft.

19. The surgical appliance as claimed in claim 13, wherein the first shaped body has a rounded, edgeless transitions to the first cross-sectional reduction.

20. The surgical appliance as claimed in claim 18, wherein the second shaped body has a rounded, edgeless transitions to the second cross-sectional reduction.

* * * * *